(12) United States Patent
Dacosta et al.

(10) Patent No.: US 11,925,364 B2
(45) Date of Patent: Mar. 12, 2024

(54) IMPLANT, ALIGNMENT GUIDES, SYSTEM AND METHODS OF USE

(71) Applicant: Paragon 28, Inc., Englewood, CO (US)

(72) Inventors: Albert Dacosta, Lone Tree, CO (US); Randy Allard, Golden, CO (US); Richard David Hunt, Arvada, CO (US); Laura Zagrocki Brinker, Lone Tree, CO (US); Spanky Raymond, Uniontown, OH (US)

(73) Assignee: Paragon 28, Inc., Englewood, CO (US)

( * ) Notice: Subject to any disclaimer, the term of this patent is extended or adjusted under 35 U.S.C. 154(b) by 225 days.

(21) Appl. No.: 17/445,044

(22) Filed: Aug. 13, 2021

(65) Prior Publication Data
US 2022/0000496 A1 Jan. 6, 2022

Related U.S. Application Data

(63) Continuation of application No. PCT/US2020/018086, filed on Feb. 13, 2020.
(Continued)

(51) Int. Cl.
*A61B 17/17* (2006.01)
*A61B 17/56* (2006.01)
(Continued)

(52) U.S. Cl.
CPC ...... *A61B 17/1728* (2013.01); *A61B 17/8004* (2013.01); *A61B 17/8057* (2013.01);
(Continued)

(58) Field of Classification Search
CPC ............ A61B 17/1728; A61B 17/8004; A61B 17/8057; A61B 17/842; A61B 17/86;
(Continued)

(56) References Cited

U.S. PATENT DOCUMENTS 2,526,959 A 10/1950 Lorenzo
4,790,302 A 12/1988 Colwill
(Continued)

FOREIGN PATENT DOCUMENTS

EP 1273271 8/2007
FR 3030221 6/2016
(Continued)

OTHER PUBLICATIONS

Budny et al. "Naviculocuneiform Arthrodesis," Clinics in Podiatric Medicine and Surgery, vol. 24, pp. 753-763, Oct. 2007.
(Continued)

*Primary Examiner* — Kevin T Truong
*Assistant Examiner* — Diana Jones
(74) *Attorney, Agent, or Firm* — Heslin Rothenberg Farley & Mesiti PC; Jacquelyn A. Graff, Esq.

(57) ABSTRACT

Bone fusion system, devices, guides, implant and methods for using the bone fusion system, devices, guides and implant are disclosed. The fusion system includes a first alignment guide, a second alignment guide, and an implant. The first alignment guide couples to an intermediate portion of the implant and the second alignment guide couples to a distal portion of the implant. The implant includes a body portion, a first extension portion extending away from a first end of the body portion, a second extension portion extending away from a posterior of the body portion, and a third extension portion extending away from a distal end of the body portion. Finally, methods for using the bone fusion system, devices, guide and implant are disclosed.

20 Claims, 26 Drawing Sheets

Related U.S. Application Data

(60) Provisional application No. 62/888,431, filed on Aug. 16, 2019, provisional application No. 62/805,081, filed on Feb. 13, 2019.

(51) Int. Cl.
  *A61B 17/80* (2006.01)
  *A61B 17/84* (2006.01)
  *A61B 17/86* (2006.01)
  *A61B 90/00* (2016.01)

(52) U.S. Cl.
  CPC ............ *A61B 17/842* (2013.01); *A61B 17/86* (2013.01); *A61B 2017/564* (2013.01); *A61B 17/8061* (2013.01); *A61B 2090/08021* (2016.02)

(58) Field of Classification Search
  CPC ...... A61B 2090/08021; A61B 17/8061; A61B 2017/564
  See application file for complete search history.

(56) References Cited

U.S. PATENT DOCUMENTS

| | | | |
|---|---|---|---|
| 5,098,435 | A | 3/1992 | Stednitz |
| 5,350,380 | A | 9/1994 | Goble |
| 5,352,228 | A | 10/1994 | Kummer |
| 5,429,641 | A | 7/1995 | Gotfried |
| 5,458,602 | A | 10/1995 | Goble |
| 5,688,284 | A | 11/1997 | Chervitz |
| 6,342,057 | B1 | 1/2002 | Brace |
| 6,692,496 | B1 | 2/2004 | Wardlaw |
| 7,011,665 | B2 | 3/2006 | Null |
| 7,316,687 | B2 | 1/2008 | Aikins |
| 7,785,326 | B2 | 8/2010 | Green |
| 7,819,877 | B2 | 10/2010 | Guzman |
| 8,206,389 | B2 | 6/2012 | Huebner |
| 8,231,627 | B2 | 7/2012 | Huebner |
| 8,337,503 | B2 | 12/2012 | Lian |
| 8,535,355 | B2 | 9/2013 | Prasad |
| 8,821,508 | B2 | 9/2014 | Medoff |
| 9,044,250 | B2 | 6/2015 | Olsen |
| 9,119,721 | B2 | 9/2015 | Sharkey et al. |
| 9,161,796 | B2 | 10/2015 | Chiodo |
| 9,241,744 | B2 | 1/2016 | Blake |
| 9,421,103 | B2 | 8/2016 | Jeng et al. |
| 2003/0009217 | A1 | 1/2003 | McKernan |
| 2004/0102776 | A1 | 5/2004 | Huebner |
| 2004/0102777 | A1 | 5/2004 | Huebner |
| 2004/0181221 | A1 | 9/2004 | Huebner |
| 2004/0193165 | A1 | 9/2004 | Orbay |
| 2005/0027296 | A1 | 2/2005 | Thramann |
| 2005/0033301 | A1 | 2/2005 | Lombardo |
| 2005/0216008 | A1 | 9/2005 | Zwirnmann |
| 2005/0234472 | A1 | 10/2005 | Huebner |
| 2006/0069394 | A1 | 3/2006 | Weiler |
| 2006/0189996 | A1 | 8/2006 | Orbay |
| 2007/0173843 | A1 | 7/2007 | Matityahu |
| 2007/0225714 | A1 | 9/2007 | Gradl |
| 2007/0239168 | A1 | 10/2007 | Kuenzi |
| 2007/0270850 | A1 | 11/2007 | Geissler |
| 2008/0015590 | A1 | 1/2008 | Sanders |
| 2008/0091197 | A1 | 4/2008 | Coughlin |
| 2008/0188852 | A1 | 8/2008 | Matityahu |
| 2009/0036931 | A1 | 2/2009 | Pech |
| 2009/0088767 | A1 | 4/2009 | Leyden |
| 2009/0093849 | A1 | 4/2009 | Grabowski |
| 2009/0157086 | A1 | 6/2009 | Digeser |
| 2009/0171398 | A1 | 7/2009 | Phillips |
| 2010/0087824 | A1 | 4/2010 | Collazo |
| 2010/0121324 | A1 | 5/2010 | Tyber |
| 2010/0179597 | A1 | 7/2010 | Henderson |
| 2011/0046681 | A1 | 2/2011 | Prandi |
| 2011/0144647 | A1 | 6/2011 | Appenzeller |
| 2011/0144700 | A1 | 6/2011 | Konieczynski |
| 2011/0218576 | A1 | 9/2011 | Galm |
| 2011/0224734 | A1 | 9/2011 | Schelling |
| 2011/0264149 | A1 | 10/2011 | Pappalardo |
| 2011/0270319 | A1 | 11/2011 | Sheffer |
| 2011/0282397 | A1 | 11/2011 | Richter |
| 2012/0078252 | A1 | 3/2012 | Huebner |
| 2012/0109217 | A1 | 5/2012 | Perineau |
| 2012/0209268 | A1 | 8/2012 | Overes |
| 2012/0253347 | A1 | 10/2012 | Murashko, Jr. |
| 2012/0271314 | A1 | 10/2012 | Stemniski |
| 2012/0303038 | A1 | 11/2012 | Durante |
| 2012/0316562 | A1 | 12/2012 | Costa |
| 2013/0018424 | A1 | 1/2013 | Subik |
| 2013/0150903 | A1 | 6/2013 | Vincent |
| 2013/0172942 | A1 | 7/2013 | Lewis et al. |
| 2013/0325076 | A1 | 12/2013 | Palmer |
| 2014/0066996 | A1 | 3/2014 | Price et al. |
| 2014/0107798 | A1 | 4/2014 | Jeng et al. |
| 2014/0114322 | A1 | 4/2014 | Perez, III |
| 2014/0180348 | A1* | 6/2014 | Thoren ................ A61B 17/17 606/86 R |
| 2015/0032168 | A1 | 1/2015 | Orsak |
| 2015/0150683 | A1 | 6/2015 | Donner et al. |
| 2015/0182267 | A1 | 7/2015 | Wolf et al. |
| 2015/0245923 | A1 | 9/2015 | Abdou |
| 2015/0359580 | A1* | 12/2015 | Dacosta ................ A61B 17/17 606/281 |
| 2016/0030064 | A1 | 2/2016 | Dacosta et al. |
| 2016/0135858 | A1 | 5/2016 | Dacosta et al. |
| 2016/0235414 | A1 | 8/2016 | Hatch et al. |
| 2016/0310191 | A1 | 10/2016 | Seykora |
| 2016/0324552 | A1 | 11/2016 | Baker et al. |
| 2016/0354128 | A1* | 12/2016 | Jeng ................ A61B 17/1728 |
| 2017/0000534 | A1 | 1/2017 | Medoff |
| 2017/0056031 | A1 | 3/2017 | Awtrey et al. |
| 2017/0216043 | A1 | 8/2017 | Surma et al. |
| 2018/0110530 | A1 | 4/2018 | Wagner et al. |
| 2018/0242987 | A1 | 8/2018 | Lintula et al. |
| 2018/0242988 | A1 | 8/2018 | Dacosta et al. |
| 2018/0280069 | A1 | 10/2018 | Barmes et al. |
| 2019/0015140 | A1 | 1/2019 | Dacosta et al. |
| 2019/0038326 | A1 | 2/2019 | Hedgeland et al. |

FOREIGN PATENT DOCUMENTS

| | | |
|---|---|---|
| JP | 04250156 | 9/1992 |
| JP | 2009112594 | 5/2009 |
| WO | 1994015556 | 7/1994 |
| WO | 2005089660 | 9/2005 |
| WO | 2009052294 | 4/2009 |
| WO | 2012103335 | 8/2012 |
| WO | 2012106477 | 8/2012 |
| WO | 2015138542 | 9/2015 |
| WO | 2017004221 | 1/2017 |
| WO | 2017011656 | 1/2017 |

OTHER PUBLICATIONS

Kamat et al. "Laparoscopic extraction of fractured Kirschner wire from the pelvis," Journal of Minimal Access Surgery, vol. 10, No. 2, pp. 97-98, Jun. 2014.

International Search Report and Written Opinion of the International Searching Authority for PCT/US2020/018086, dated May 11, 2020, 17 pages.

Extended European Search Report issued in European Patent Application No. 20755498.1, dated Oct. 21, 2022, 9 pages.

* cited by examiner

IMPLANT, ALIGNMENT GUIDES, SYSTEM AND METHODS OF USE

CROSS-REFERENCE TO RELATED APPLICATIONS

This application is a continuation of PCT/US2020/018086 filed Feb. 13, 2020 and entitled Implant, Alignment Guides, System and Methods of Use, which claims priority benefit under 35 U.S.C. § 119(e) of U.S. Provisional Application No. 62/805,081 filed Feb. 13, 2019, entitled Optimizing Anterior Tibiotalar (TT) and Lateral Tibiotalocalcaneal (TTC) Plate Thickness for Avoidance of Stress Shielding and Implant Breakage, and U.S. Provisional Application No. 62/888,431 filed Aug. 16, 2019, entitled Implant, Alignment Guides, System and Methods of Use, which are incorporated herein by reference in their entireties.

FIELD OF INVENTION

The present disclosure relates generally to general surgery and orthopaedic implants used for achieving bone fusion. More specifically, but not exclusively, the present disclosure relates to surgical devices, implants, guides, and systems for fixation of human bones, such as, the foot and ankle bones, and to stabilize the realignment of a fracture, dislocation, fusion or the like of the bones of the foot and ankle.

BACKGROUND OF THE INVENTION

Currently available guides and systems for foot and ankle fusion surgeries include fixed trajectories for insertion of fasteners to fuse the patient's bones. The currently available guides and systems limit a surgeon's options and do not allow for adjustment based on each patient's unique anatomy.

Accordingly, it is an object of the present disclosure to overcome one or more of the above-described drawbacks and/or disadvantages of the currently used procedures. For example, in view of the deficiencies of the currently available implants, guides, systems and methods it would be desirable to develop implants, guides, systems and methods that allow for adjustment of the fastener insertion trajectories to overcome the above-noted drawbacks of the currently available systems and surgical solutions.

SUMMARY OF THE INVENTION

Aspects of the present disclosure provide bone fixation devices for use in a method of fusing bones. Specifically, the present disclosure relates to surgical devices, implants, guides, systems and methods for fixation of human bones, such as, the foot and ankle bones, and to stabilize realignment of a fracture, dislocation, fusion or the like of the foot or ankle bones.

In one aspect, provided herein is a fusion system, including a first alignment guide, a second alignment guide, and an implant, wherein the first alignment guide couples to an intermediate portion of the implant and the second alignment guide couples to a distal portion of the implant.

In another aspect, provided herein is an implant, including a body portion, a first extension portion extending away from a first end of the body portion, a second extension portion extending away from a second end of the body portion, and a third extension portion extending posteriorly away from the second end of the body portion.

In a further aspect, provided herein is a method for using a fusion system, preparing at least one joint and inserting fixation wires across the at least one joint. The method may also include obtaining a plate and placing the plate over a first bone and at least one second bone of the at least one joint. The method may further include coupling the plate to the first bone and the at least one second bone. In addition, the method includes obtaining a first alignment guide and coupling the first alignment guide to the plate. Next, the method includes inserting a first k-wire through the first alignment guide and across a first joint of the at least one joint. Further, the method includes obtaining a second alignment guide and coupling the second alignment guide to the plate. Then, the method includes inserting a second k-wire through the second alignment guide and across a second joint of the at least one joint. The method also includes removing the first alignment guide from the plate and removing the second alignment guide from the plate. The method further includes inserting a first compression fastener across the first joint and inserting a second compression fastener across the second joint. Finally, the method includes removing the k-wire and closing an incision.

These, and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. The drawings are only for purposes of illustrating preferred embodiments and are not to be construed as limiting the disclosure. It is emphasized that, in accordance with the standard practice in the industry, various features are not drawn to scale. In fact, the dimensions of the various features may be arbitrarily increased or reduced for clarity of discussion. The foregoing and other objects, features and advantages of the disclosure are apparent from the following detailed description taken in conjunction with the accompanying drawings in which.

DETAILED DESCRIPTION OF THE INVENTION

Figure 1:
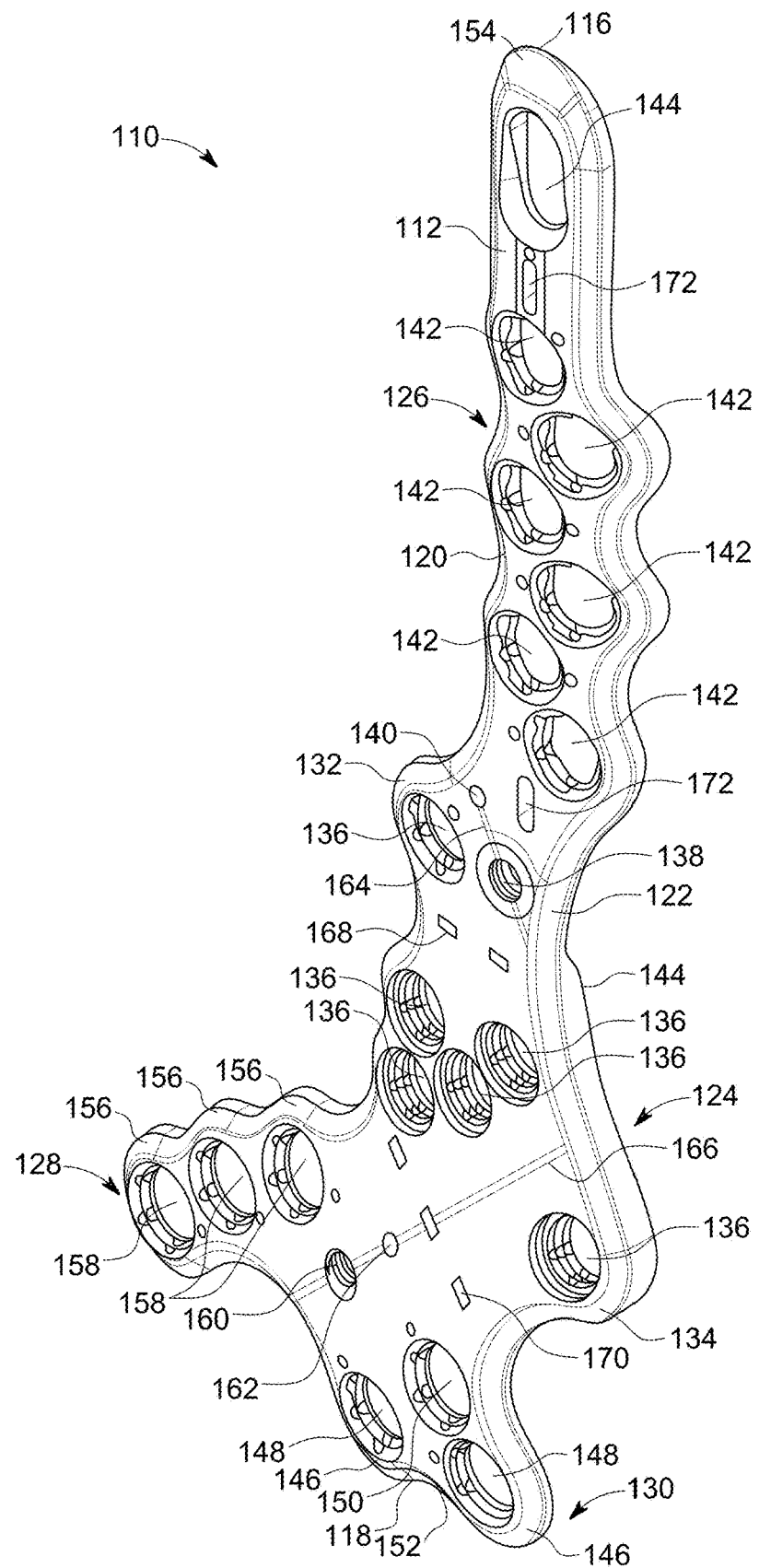
FIG. 1 is a first front perspective view of an implant, in accordance with an aspect of the present disclosure.
Figure 2:
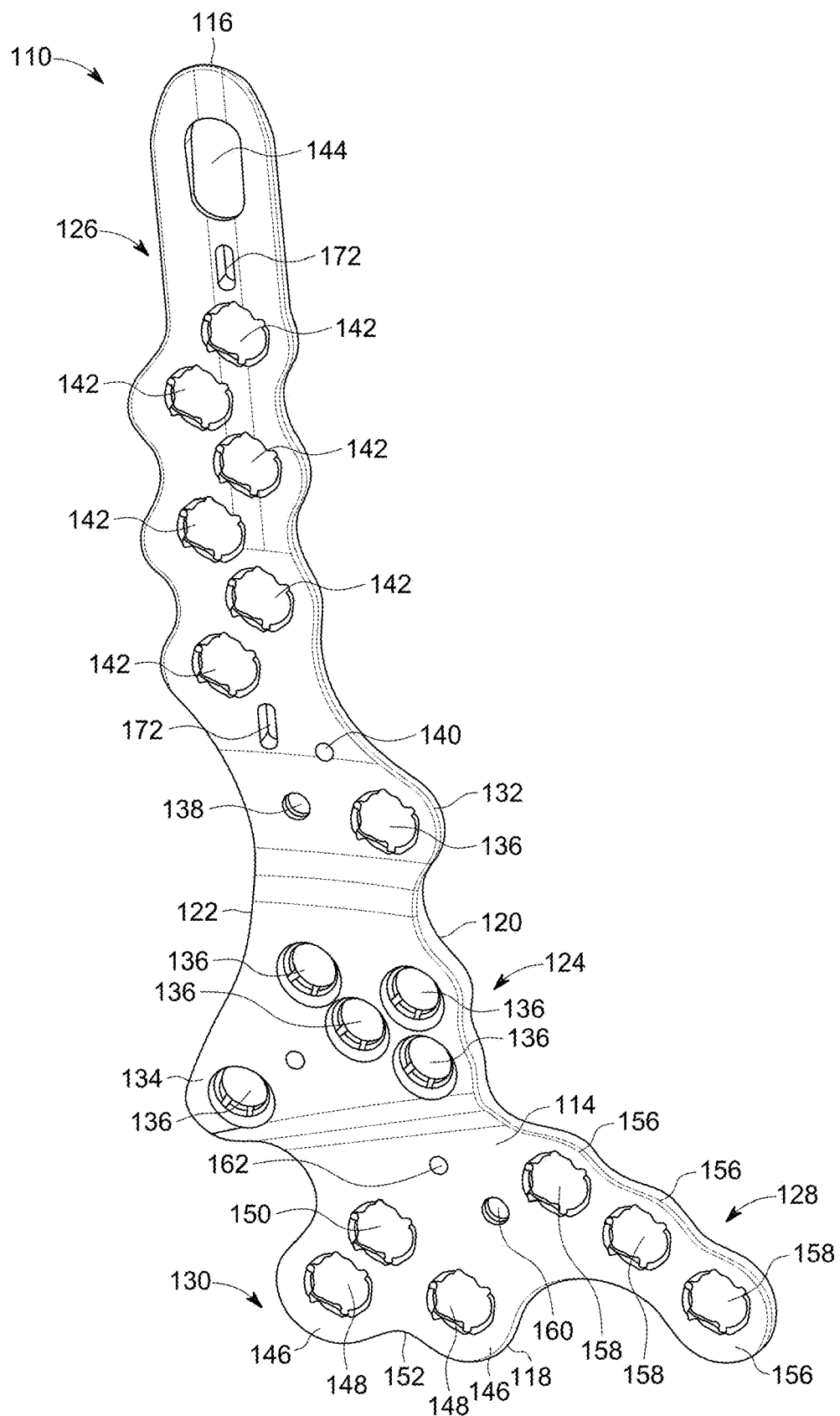
FIG. 2 is a first back perspective view of the implant of FIG. 1, in accordance with an aspect of the present disclosure.
Figure 3:
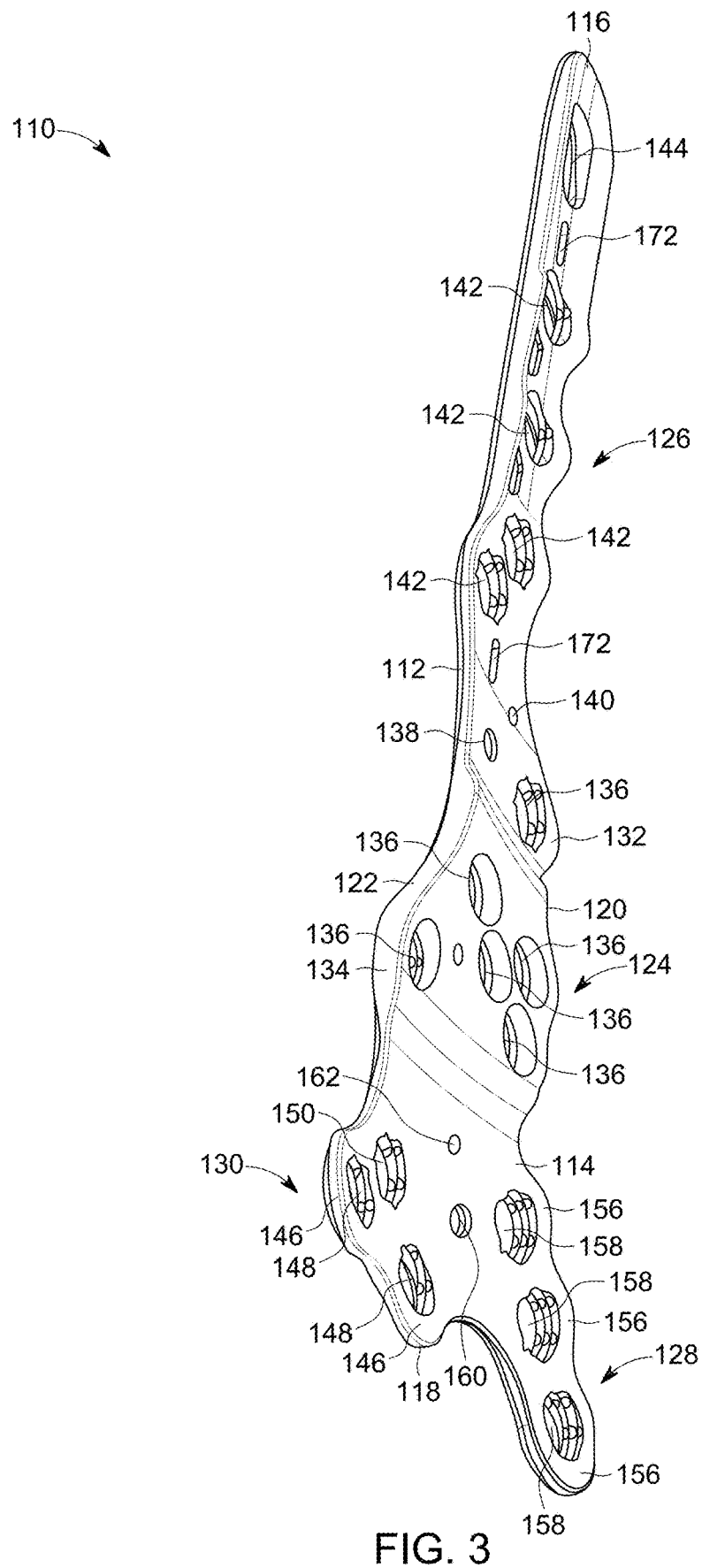
FIG. 3 is a second back perspective view of the implant of FIG. 1, in accordance with an aspect of the present disclosure.
Figure 4:
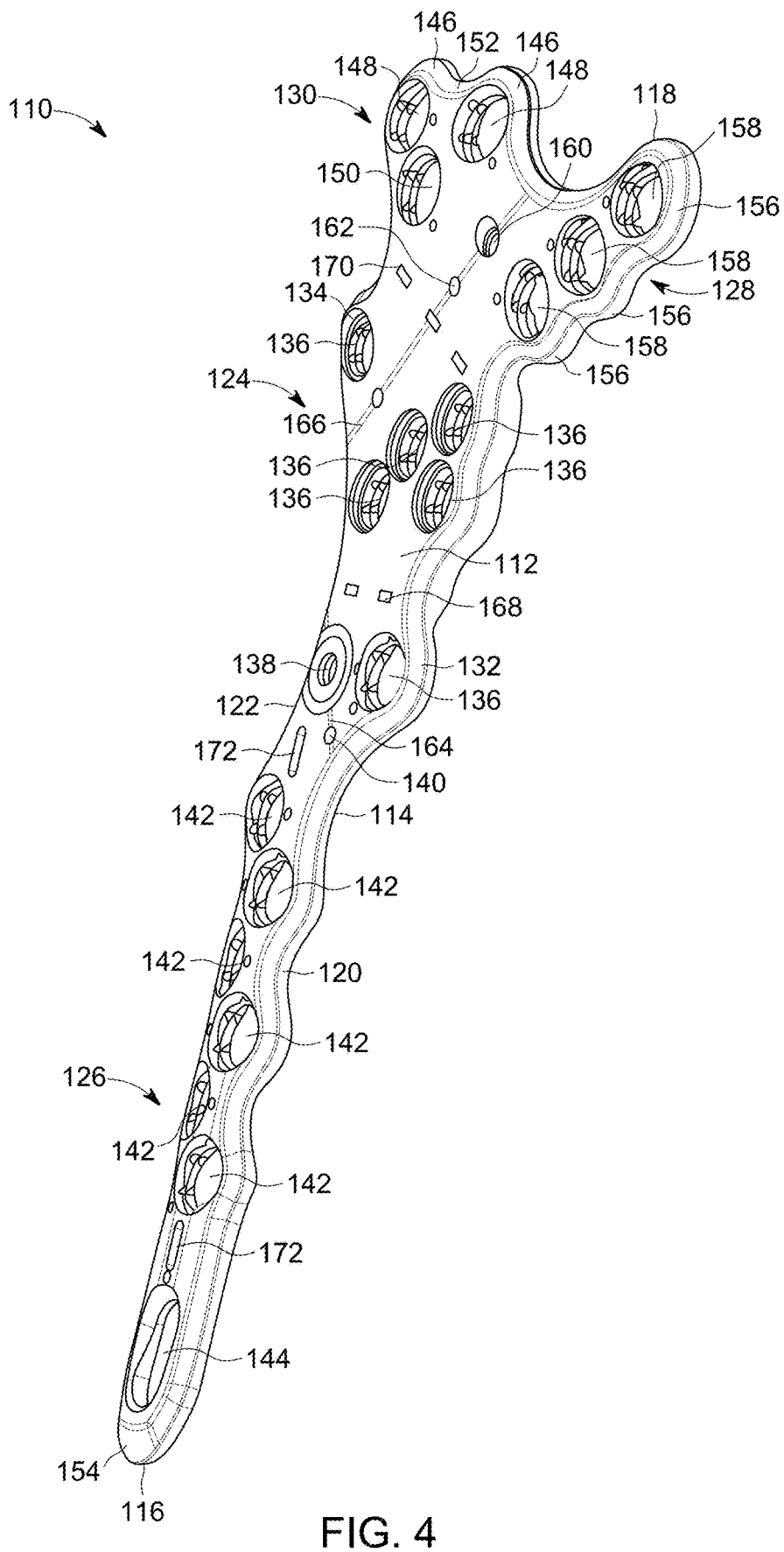
FIG. 4 is a second front perspective view of the implant of FIG. 1, in accordance with an aspect of the present disclosure.

Generally stated, disclosed herein are embodiments of devices, implants, guides, and systems for fixation of human bones, such as, foot and ankle bones. Further, surgical methods for using the devices, implants, guides, and systems for fixation of human bones to stabilize realignment of a fracture, dislocation, fusion or the like of the foot and ankle bones are discussed.

In this detailed description and the following claims, the words proximal, distal, anterior or plantar, posterior or dorsal, medial, lateral, superior and inferior are defined by their standard usage for indicating a particular part of a bone, implant, device or guide according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices and methods are described herein with reference to use with the bones of the foot and ankle, the bones of the foot, ankle and lower leg may be used to describe the surfaces, positions, directions or orientations of the devices, instrumentation and methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices and methods, and the aspects, components, features and the like thereof, described herein with respect to the right foot and ankle may be mirrored so that they likewise function with the left foot and ankle. Further, the devices and methods, and the aspects, components, features and the like thereof, disclosed herein are described with respect to the foot and ankle for brevity purposes, but it should be understood that the devices and methods may be used with other bones of the body having similar structures, for example the upper extremity, and more specifically, with the bones of the wrist, hand, and arm.

Referring to the drawings, wherein like reference numerals are used to indicate like or analogous components throughout the several views, and with particular reference to FIGS. 1-10, an implant or plate 110 is shown. The plate 110 includes a top surface 112 opposite a bottom surface 114, a first end 116 opposite a second end 118, and a first side 120 generally opposite a second side 122. The plate 110 also includes a body portion or intermediate portion 124, a first extension portion or proximal portion 126 extending from a proximal end of the body portion 124 to the first end 116, a second extension portion or posterior portion 128 extending from a distal end of the body portion 124 posteriorly as it extends toward the second end 118, and a third extension portion or distal portion 130 extending from the distal end of the body portion 124 to the second end 118.

Figure 5:
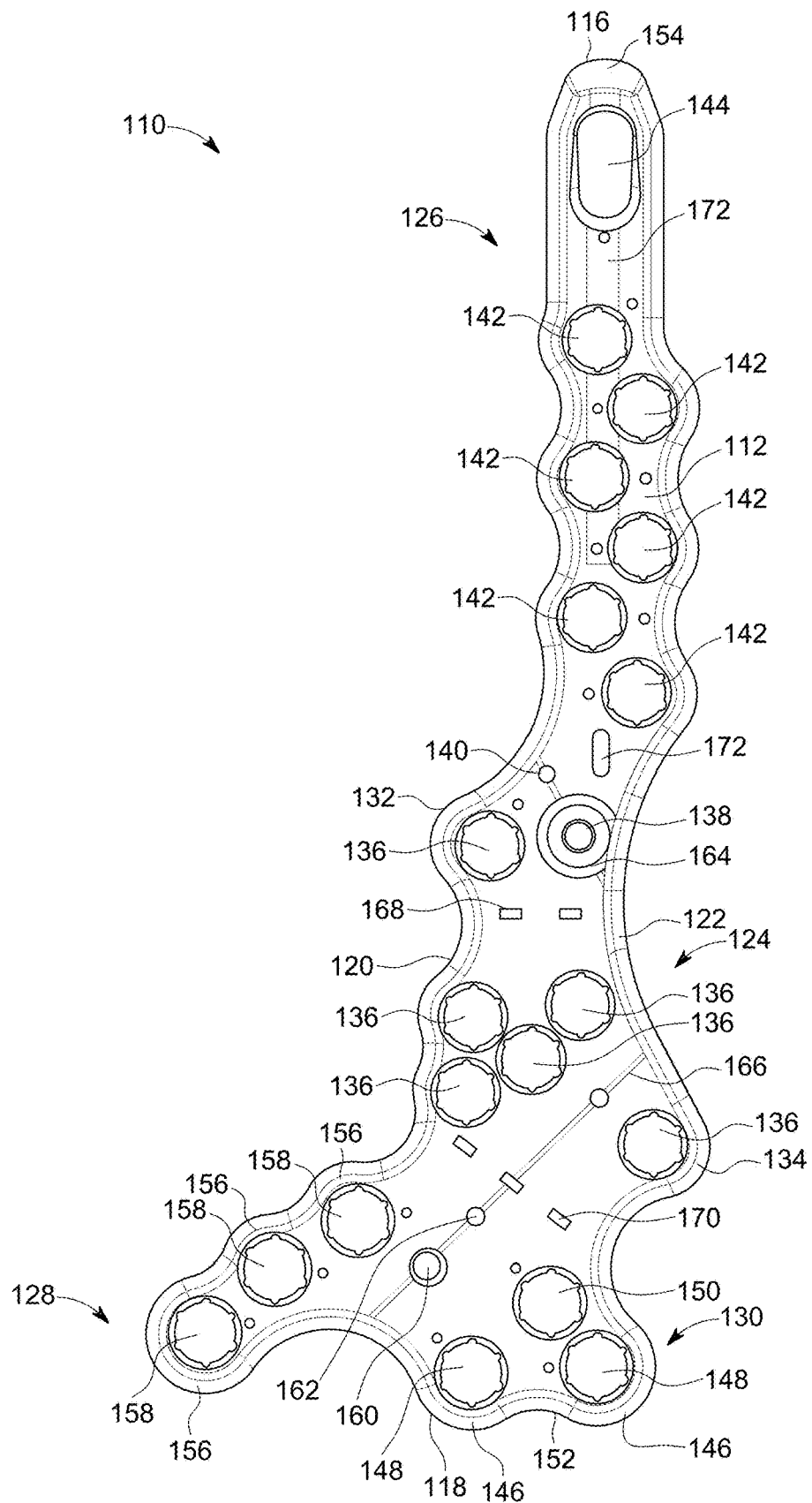
FIG. 5 is a front view of the implant of FIG. 1, in accordance with an aspect of the present disclosure.
Figure 6:
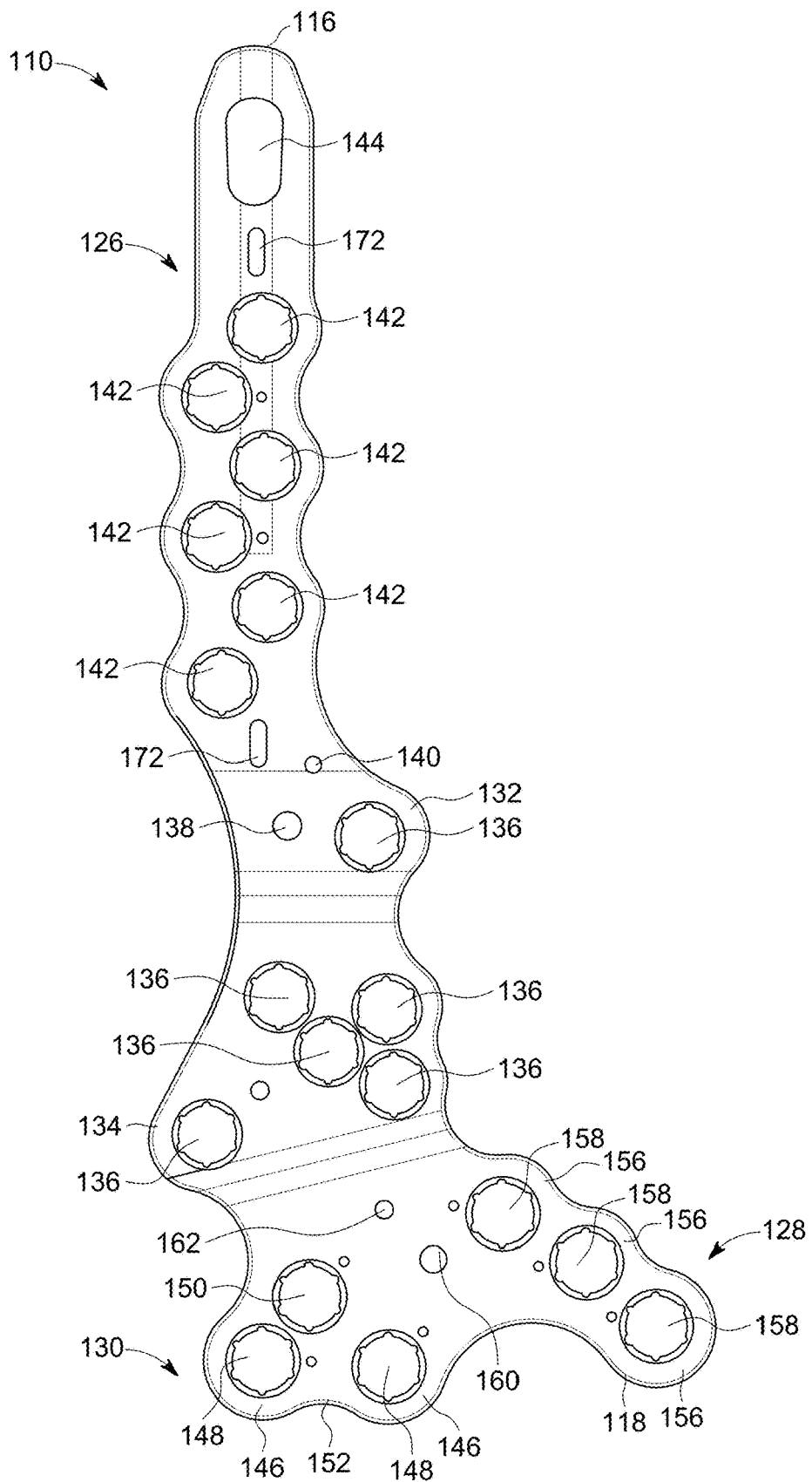
FIG. 6 is a back view of the implant of FIG. 1, in accordance with an aspect of the present disclosure.

With continued reference to FIGS. 1-10 and more specifically FIGS. 5 and 6, the body portion 124 may include at least one lobe 132, 134, for example, a first lobe 132 and a second lobe 134. The first lobe 132 may, for example, extend at least partially away from the first side 120 of the plate 110. The second lobe 134 may, for example, extend at least partially away from the second side 122 of the plate 110. Each lobe 132, 134 may include a first through hole or fastener hole 136 extending through the plate 110 from a top surface 112 to a bottom surface 114. The first through hole 136 extending through the first lobe 132 may be positioned, for example, posterior to a midline of the plate 110. The first through hole 136 extending through the second lobe 134 may be positioned, for example, anterior to the midline of the plate 110. In addition, the body portion 124 may include, for example, at least one additional first through hole 136 positioned between the first lobe 132 and the second lobe 134. As shown, the at least one through hole 136 may be, for example, four holes positioned between the first side 120 and the second side 122. Each of the first through holes 136 may be, for example, positioned in the body portion 124 to allow for fasteners 410, 412 to pass between screws 414 inserted into through holes 136 without contacting the screws 414, as shown in FIGS. 23-29.

The body portion 124 may also include a first opening or first engagement opening 138 and a second opening or first alignment opening 140 for coupling to the alignment guide 200, as shown in FIGS. 1-6 and 11-18. The first opening 138 may be, for example, offset from the second opening 140 along a longitudinal axis of the plate 110. The first opening 138 may also be positioned near the first side 120 of the plate 110 and between the first side 120 and the second opening 140. The second opening 140 may be positioned near the second side 122 of the plate 110 and between the second side 122 and the first opening 138. A first line or guide alignment marking 164 connecting the first opening 138 and second opening 140 may form an angle with respect to a midline of the plate 110 and the angle may be, for example, approximately 23° to 33°, more specifically approximately 25° to 31°, and still more specifically approximately 28°. This angle also defines the angle between the midline of the plate 110 and the longitudinal axis of the arm 212 of the alignment guide 200, as described in greater detail below. In addition, the body portion 124 may include first plate alignment markings 168 extending between the first side 120 and the second side 122. The first plate alignment markings 168 may extend, for example, generally perpendicular to the longitudinal axis of the plate 110. The first plate alignment markings 168 may be positioned, for example, below the first opening 138 and the first lobe 132.

In addition, the body portion 124 may include a third opening or second engagement opening 160 and a fourth opening or second alignment opening 162 for coupling to the alignment guide 200, as shown in FIGS. 1-6 and 11-18. The third opening 160 may be, for example, offset from the fourth opening 162 along a longitudinal axis of the plate 110. The third opening 160 may also be positioned near the posterior portion 128 of the plate 110 and between the posterior portion 128 and the fourth opening 162. The fourth opening 162 may be positioned near the distal portion 130 of the plate 110 and between the second side 122 and the third opening 160. A second line or guide alignment marking 166 connecting the third opening 160 and fourth opening 162 may form an angle with respect to a midline of the plate 110 and the angle may be, for example, approximately 41° to 51°, more specifically approximately 43° to 49°, and still more specifically approximately 46°. This angle also defines the angle between the midline of the plate 110 and the longitudinal axis of the arm 312 of the alignment guide 300, as described in greater detail below. In addition, the body portion 124 may include second plate alignment markings 170 extending between the first side 120 and the second side 122. The second plate alignment markings 170 may extend, for example, at an angle with respect to the longitudinal axis of the plate 110. The second plate alignment markings 170 may be positioned, for example, perpendicular to the second line 166 of the plate 110 and superior to the posterior portion 128 and the distal portion 130.

Figure 7:
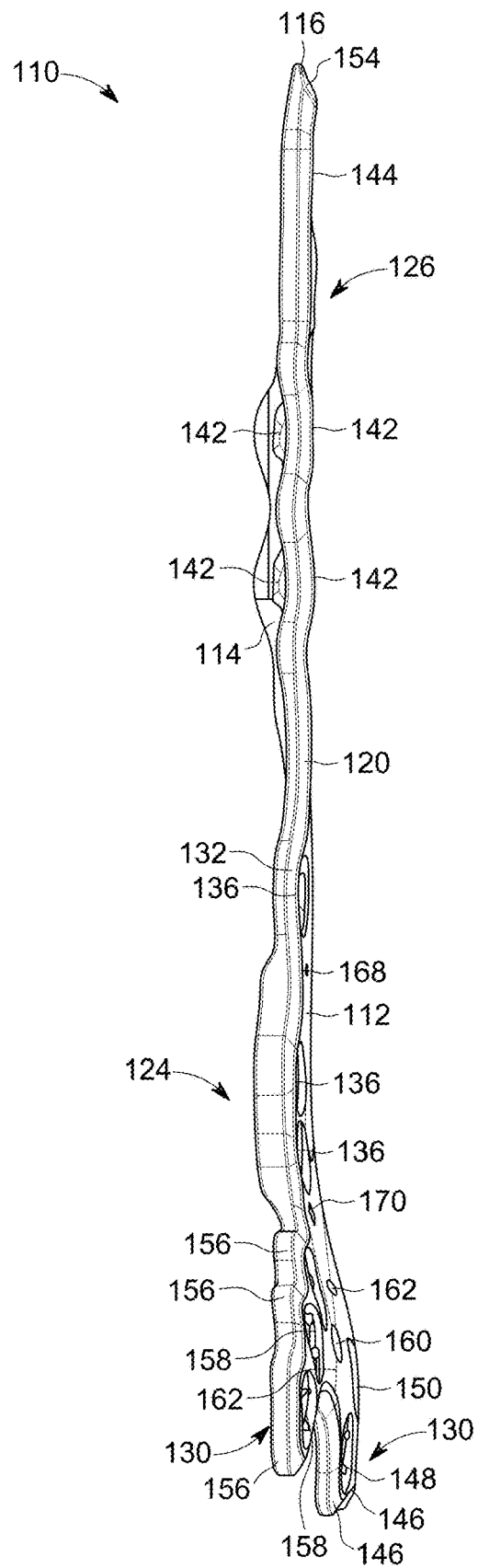
FIG. 7 is a first side view of the implant of FIG. 1, in accordance with an aspect of the present disclosure.
Figure 8:
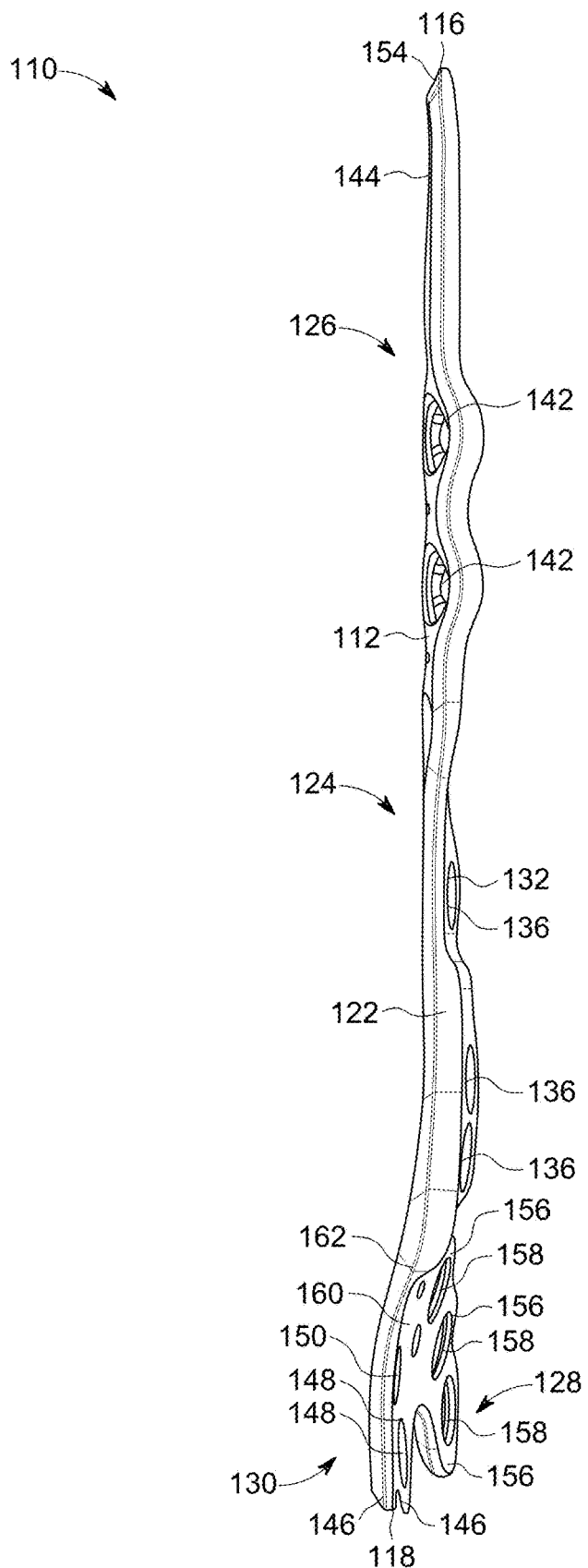
FIG. 8 is a second side view of the implant of FIG. 1, in accordance with an aspect of the present disclosure.
Figure 9:
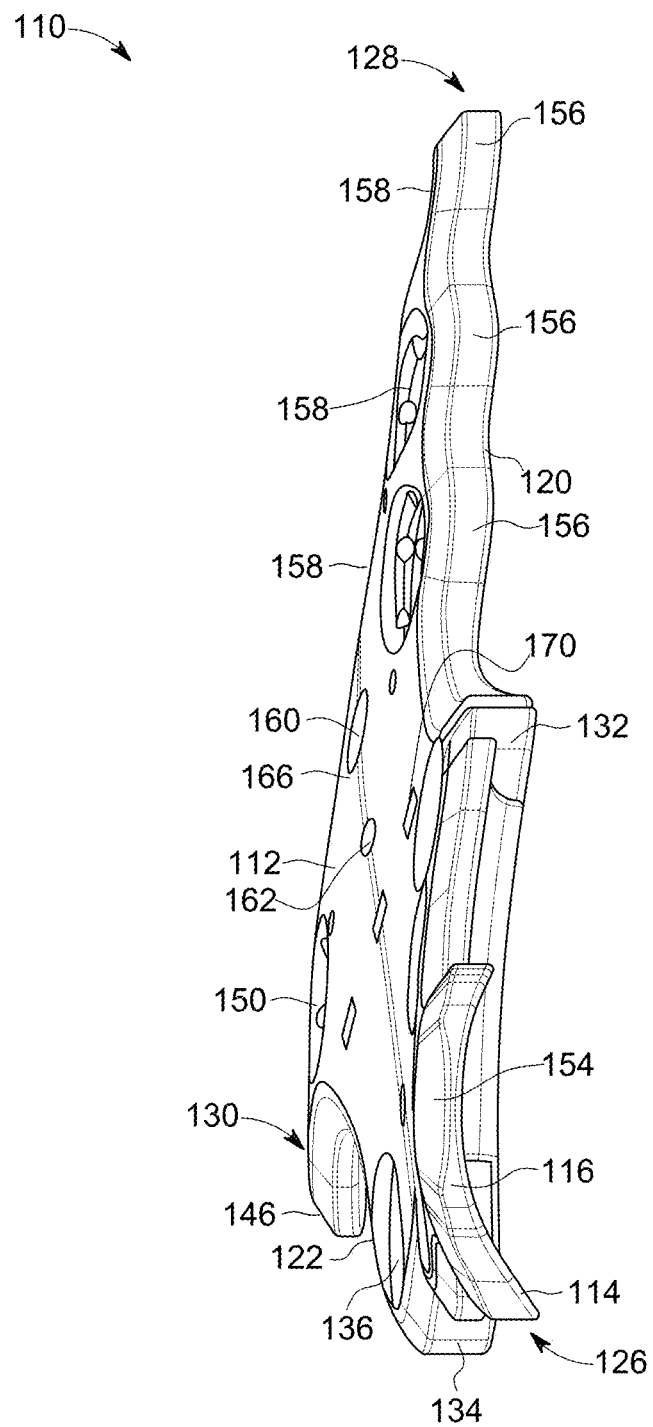
FIG. 9 is a first end view of the implant of FIG. 1, in accordance with an aspect of the present disclosure.
Figure 10:
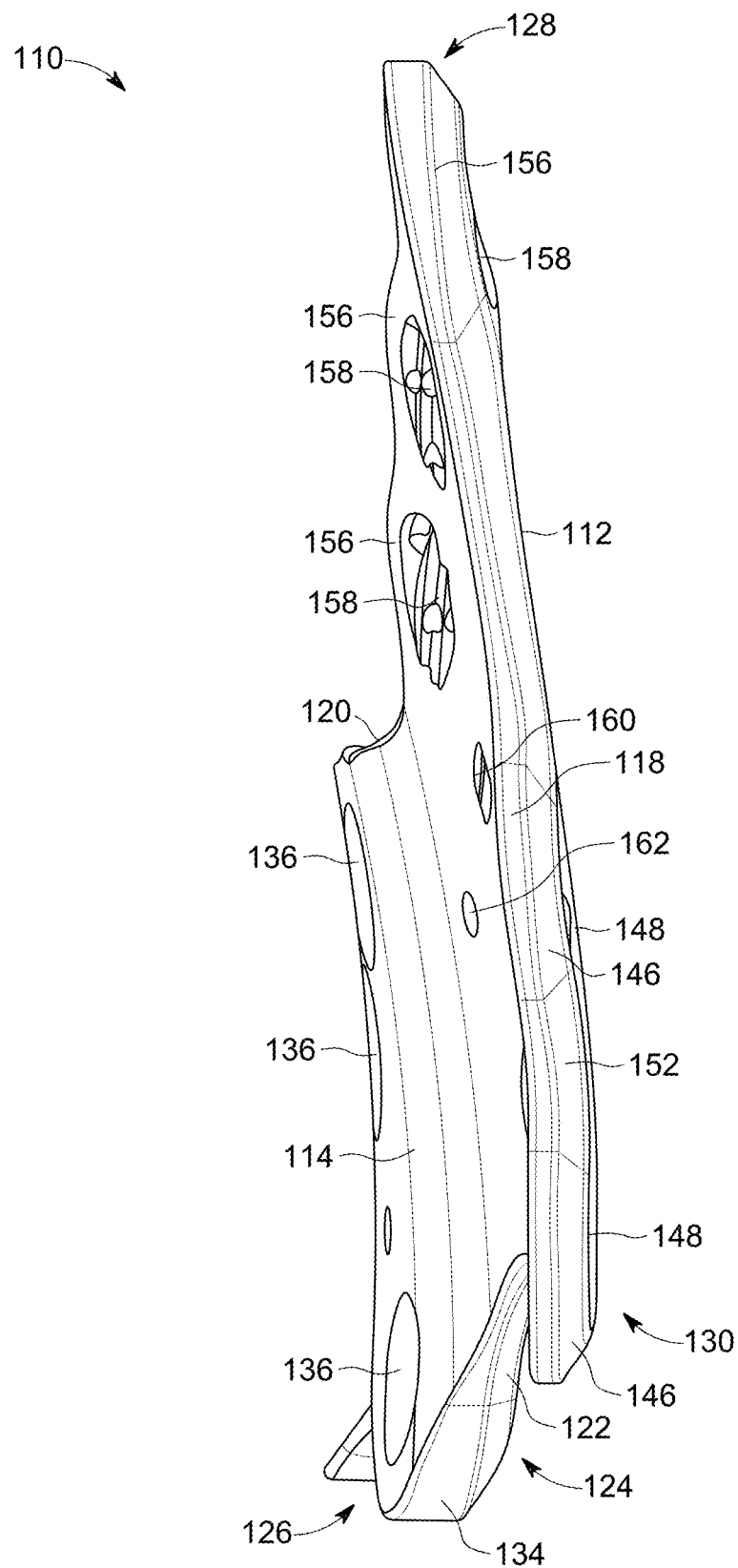
FIG. 10 is a second end view of the implant of FIG. 1, in accordance with an aspect of the present disclosure.
Figure 11:
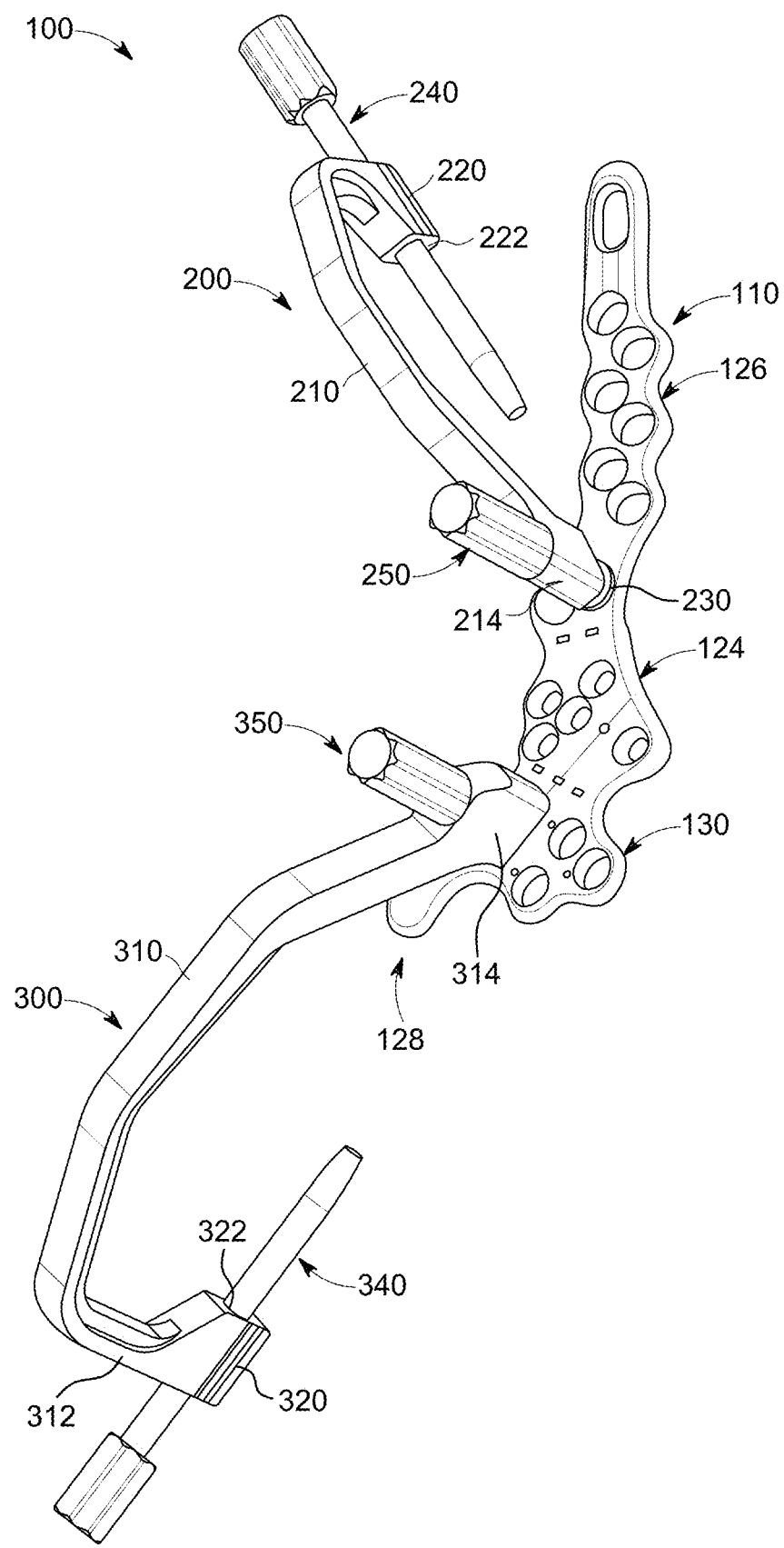
FIG. 11 is a first front perspective view of a fusion system including the implant of FIG. 1, in accordance with an aspect of the present disclosure.
Figure 12:
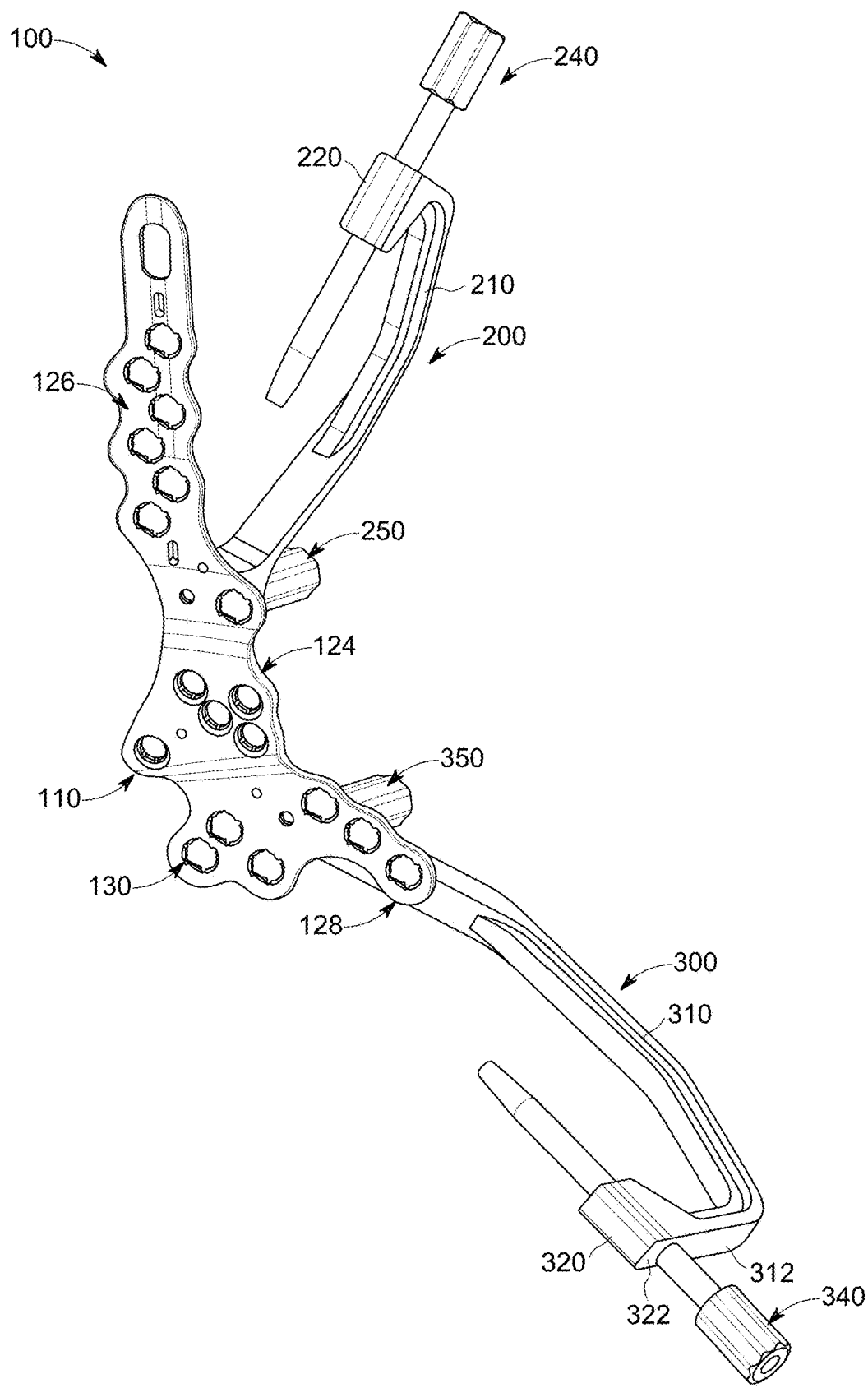
FIG. 12 is a first back perspective view of the fusion system of FIG. 11, in accordance with an aspect of the present disclosure.
Figure 13:
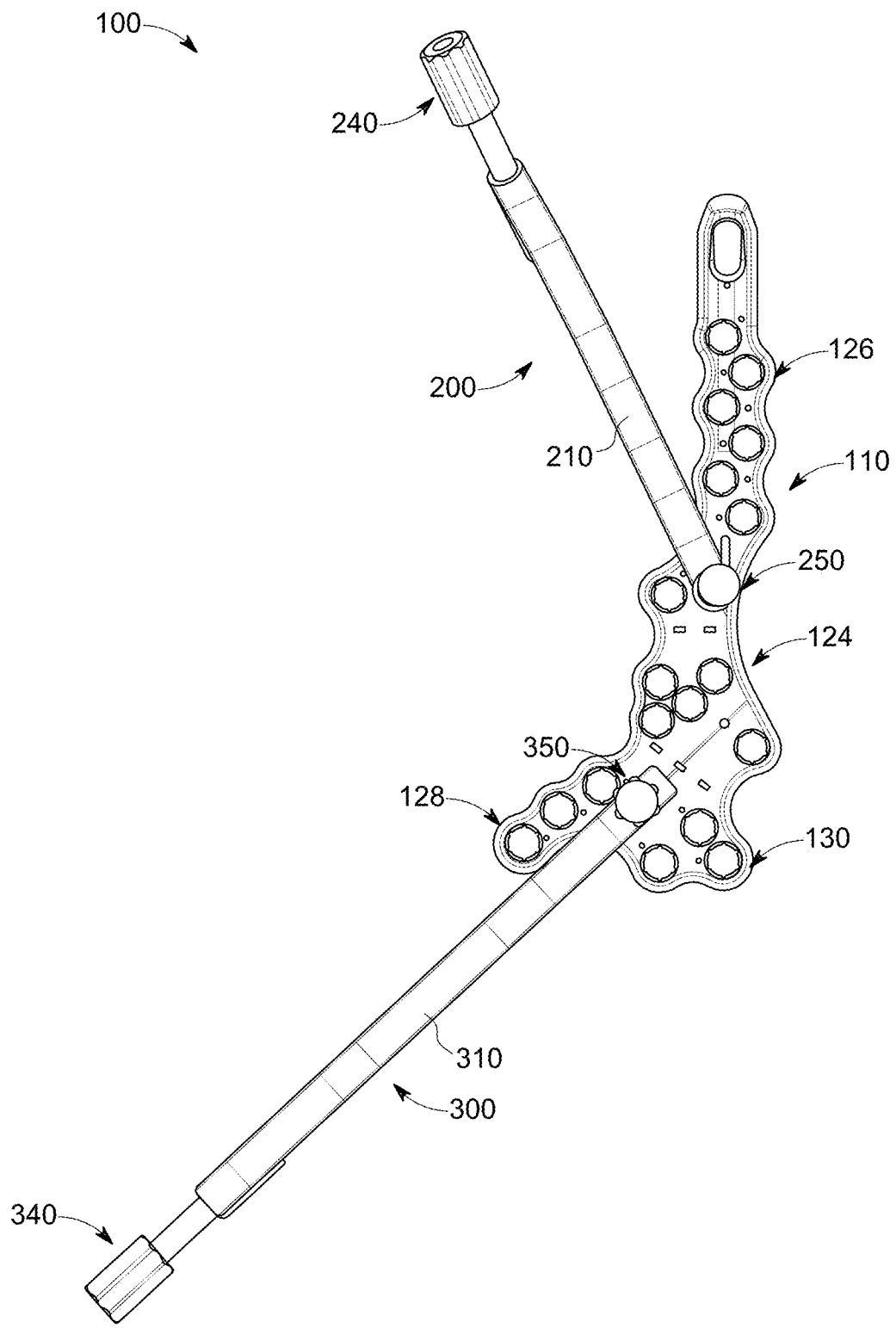
FIG. 13 is a front view of the fusion system of FIG. 11, in accordance with an aspect of the present disclosure.
Figure 14:
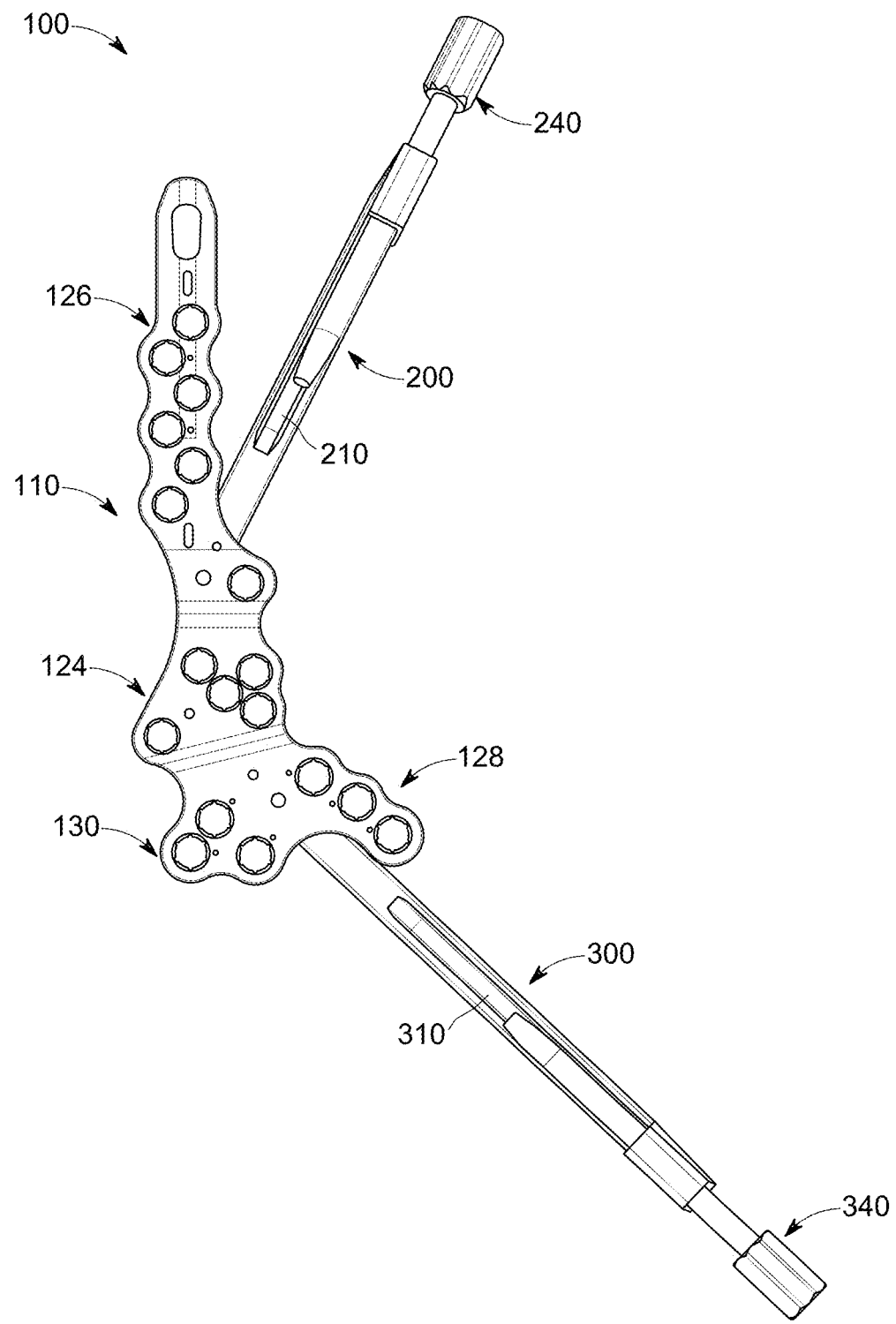
FIG. 14 is a back view of the fusion system of FIG. 11, in accordance with an aspect of the present disclosure.
Figure 15:
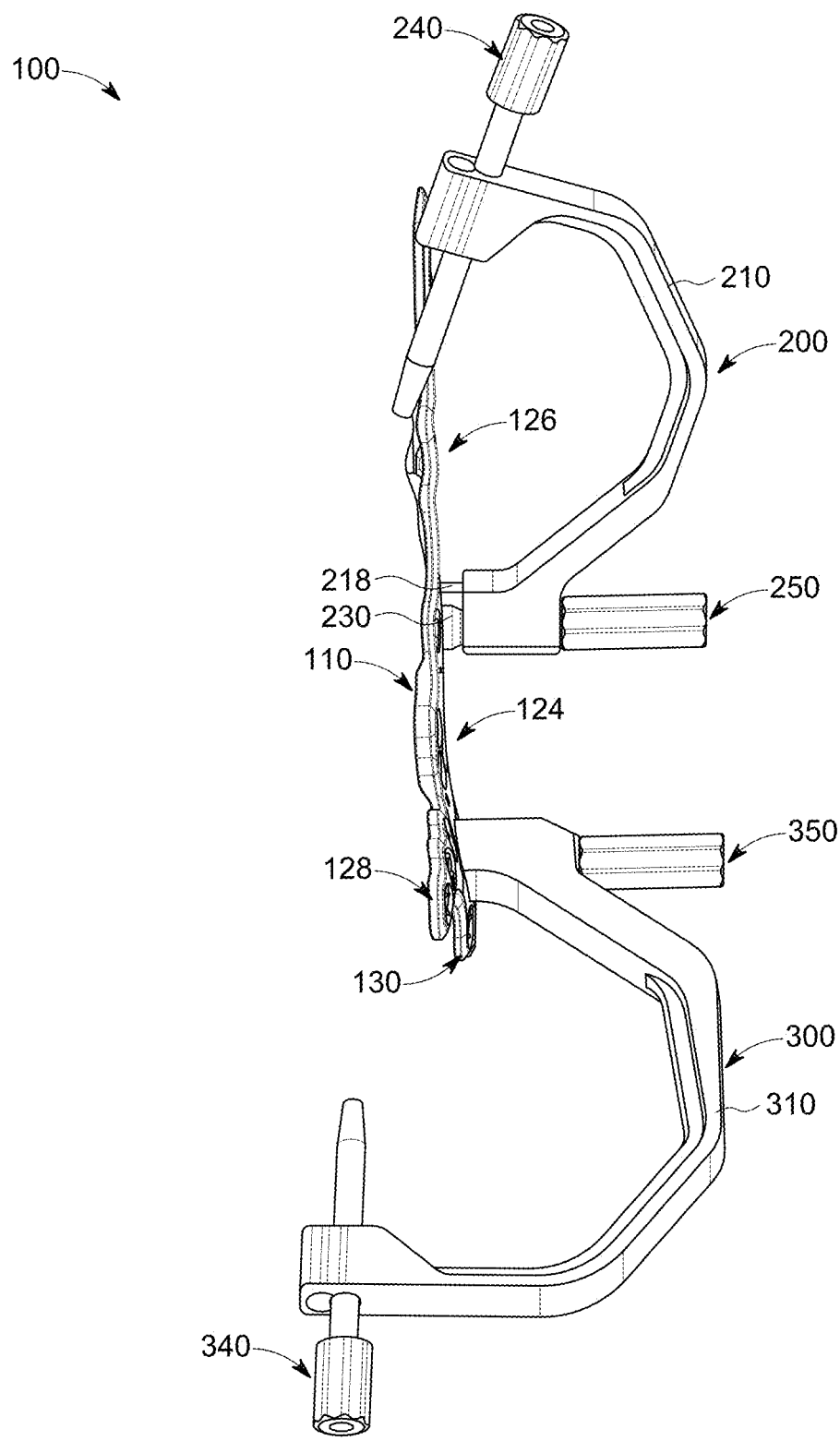
FIG. 15 is a first side view of the fusion system of FIG. 11, in accordance with an aspect of the present disclosure.
Figure 16:
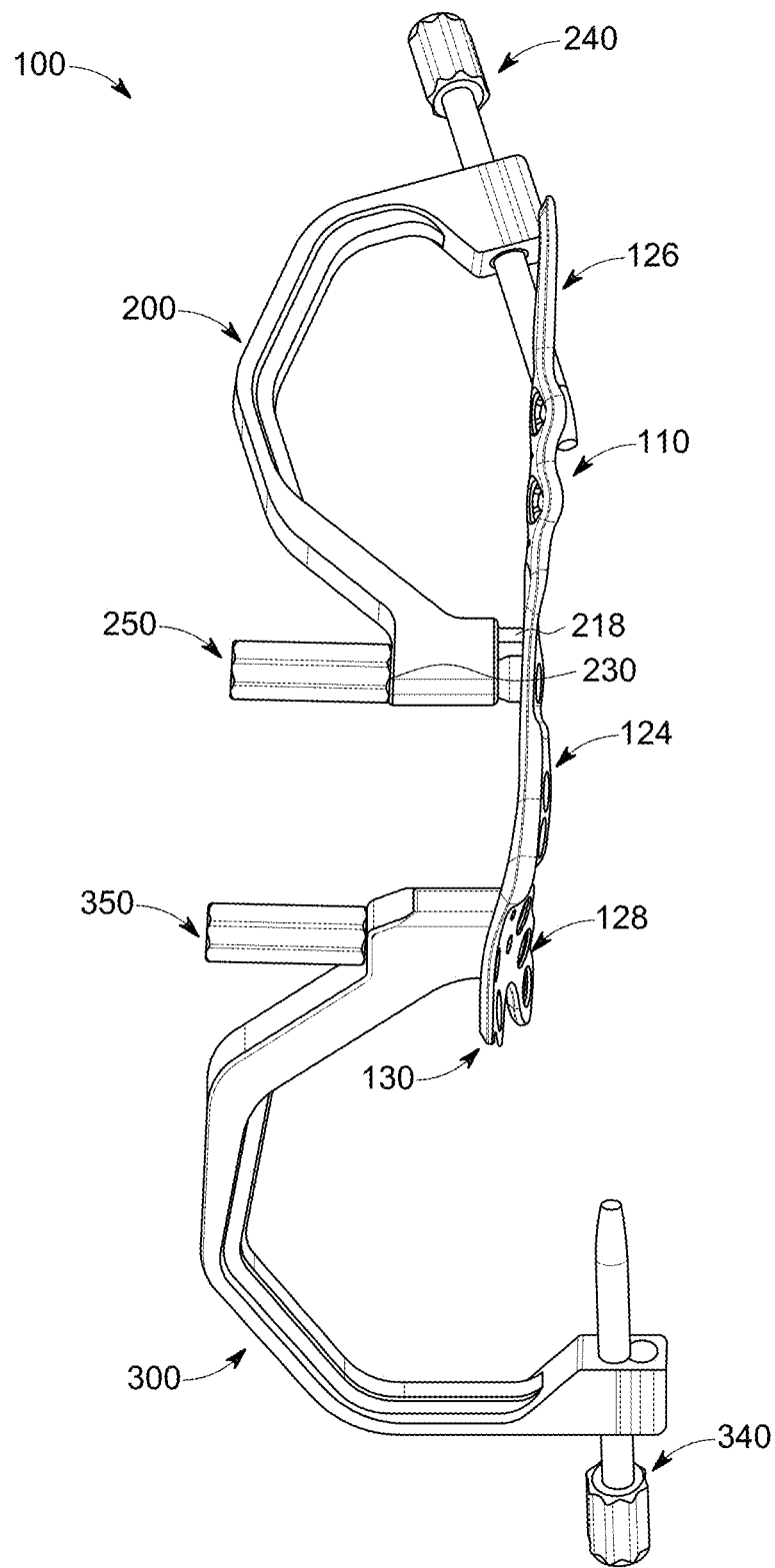
FIG. 16 is a second side view of the fusion system of FIG. 11, in accordance with an aspect of the present disclosure.
Figure 17:
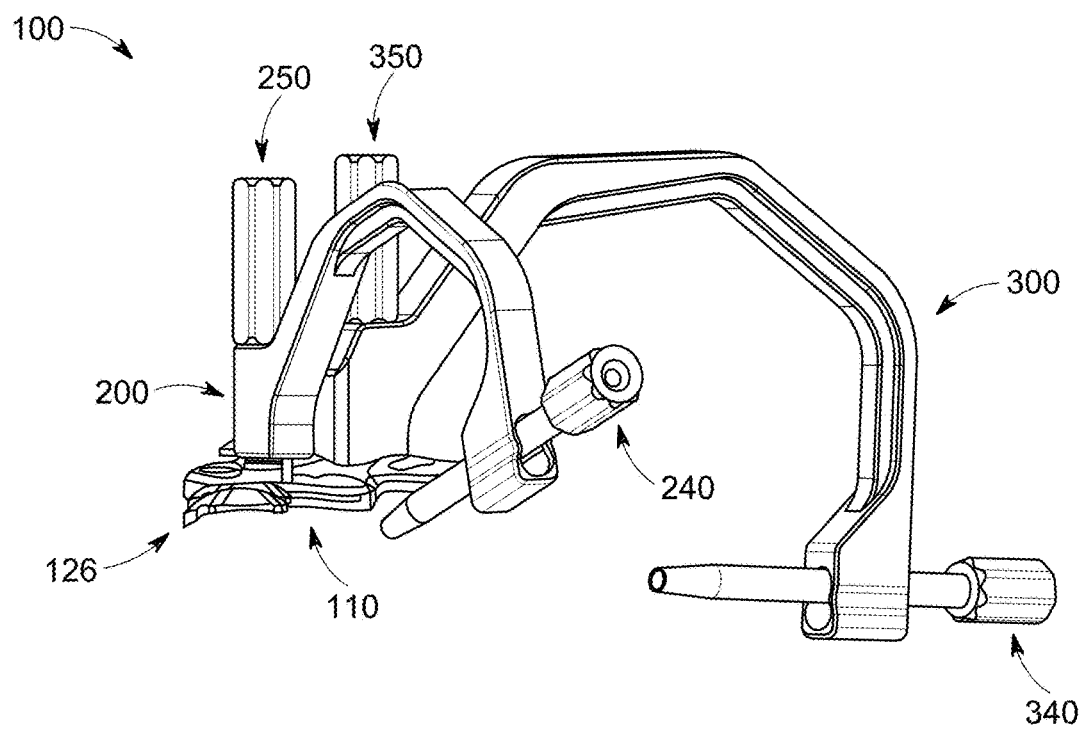
FIG. 17 is a first end view of the fusion system of FIG. 11, in accordance with an aspect of the present disclosure.
Figure 18:
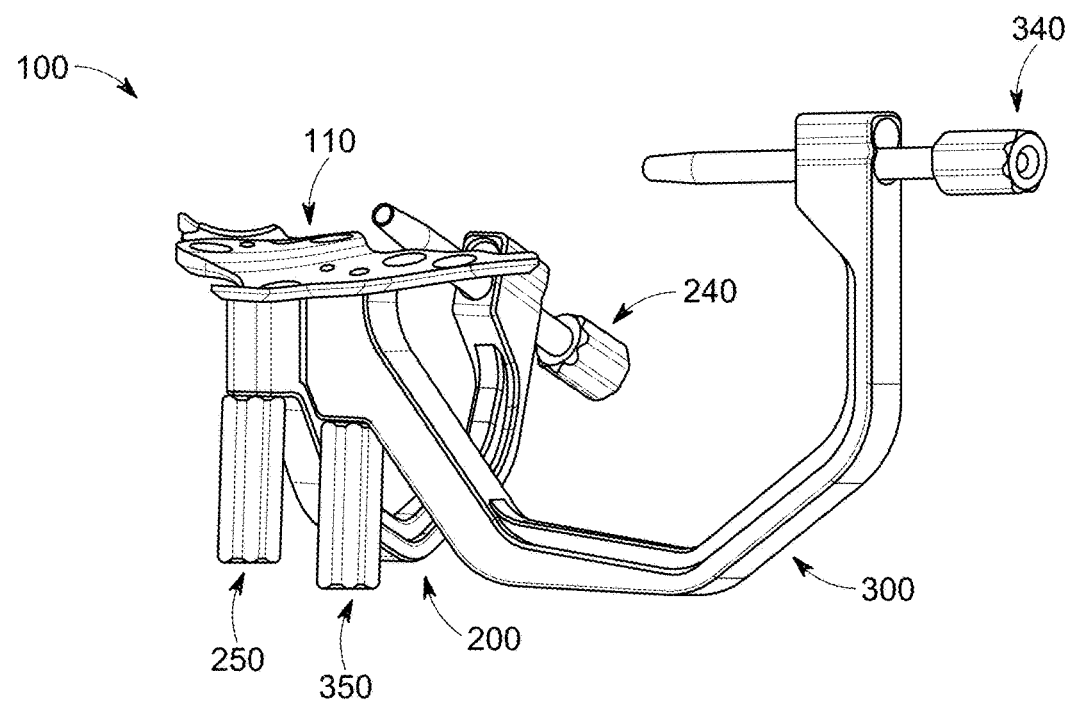
FIG. 18 is a second end view of the fusion system of FIG. 11, in accordance with an aspect of the present disclosure.

With continued reference to FIGS. 1-6 and 11-18, the body portion 124 of the plate may also be, for example, angled between the extension portion 126 or proximal end and the second lobe 134 on the second side 122 of the plate 110. The angled portion of the second side 122 may also be, for example, curved along the angle, as shown in FIGS. 5 and 6. In addition, the second side 122 may be, for example, curved between the second lobe 134 and the third extension portion or distal portion 130. Further, the first side 120 may be, for example, curved between the first lobe 132 and the second extension portion or posterior portion 128. Further, the portion between the first lobe 132 and the posterior portion 128 may include, for example, at least one additional lobe or protrusion where the intermediate through holes 136 are positioned between the first lobe 132 and the second lobe 134. Also, as shown in FIGS. 7 and 8, the body portion 124 may be, for example, curved slightly as the body portion 124 extends between the first extension portion 126 and both the posterior portion 128 and distal portion 130.

As shown in FIGS. 1, 2, 5 and 6, the extension portion 126 of the plate 110 may include at least one second through hole or fastener hole 142 positioned along the extension portion 126. As shown in the illustrated embodiment, the at least one second through hole 142 may be, for example, six second through holes 142 although alternative numbers of through holes 142 are also contemplated. The extension portion 126 may also include a slot, compression slot, or opening 144. The slot 144 may be positioned, for example, at or near the first end 116 of the plate 110. The slot 144 may be, for example, longer than the through holes 136, 142. For example, the slot 144 may have a first length along the longitudinal axis, the through holes 136, 142 may have at least one second length along the longitudinal axis, and the first length may be larger than the at least one second length. The at least one second through hole 142 may be positioned, for example, between the slot 144 and the body portion 124. The slot 144 may be, for example, positioned along the midline of the plate 110. The at least one second through hole 142 may be, for example, positioned offset from the midline of the plate 110. The extension portion 126 may also include at least one alignment slot 172. In the depicted embodiment, the extension portion 126 includes two alignment slots 172 positioned along a midline of the extension portion 126. As shown, the extension portion 126 includes a first alignment slot 172 positioned distal to the compression slot 144 and a second alignment slot 172 distal to the at least one through hole 142 and proximal to the first opening 138 and first lobe 132. The extension portion 126 may have, for example, a width that is smaller than the width of the body portion 124 and the combined width of the posterior portion 128 and distal portion 130.

Referring now to FIGS. 1-6, the posterior portion 128 may include at least one fourth lobe 156 extending away from the body portion 124 and the distal portion 130 in a posterior direction and at least one fifth through hole 158 extending through the lobe 156. As shown, the at least one fourth lobe 156 may be, for example, three lobes 156 and the at least one fifth through hole 158 may be, for example, three through holes 158. The fifth through holes 158 may extend through the plate 110 from a top surface 112 to a bottom surface 114. The fifth through holes 158 extending through the posterior portion 128 may be positioned, for example, posterior to a midline of the plate 110. Each of the lobe 156 and through hole 158 combinations may be positioned adjacent to another lobe 156 and through hole 158 combination. The lobes 156 and through holes 158 may extend, for example, linearly or curvilinear as the posterior portion 128 extends away from the plate 110.

Referring now to FIGS. 1-6, the distal portion 130 may include at least one third lobe or distal lobe 146. As depicted, the distal portion 130 includes two distal lobes 146. Each lobe 146 includes a third through hole or fastener hole 148 for receiving a fastener or bone screw 420 to secure the plate to a patient's foot, as shown in FIGS. 23-29. The through holes 148 may extend through the plate 110 from a top surface 112 to a bottom surface 114. The through hole 148 positioned near the second side 122 of the plate 110 may be, for example, positioned along the midline of the plate 110, while the through hole 148 positioned near the first side 120 of the plate 110 may be, for example, positioned posterior to the midline. The distal portion 130 may also include, for example, a ramped portion 152 positioned between the two lobes 146 to allow for surrounding tissue to slide over the distal end 118 of the plate 110 without irritating the tissue. The distal portion 130 may also include at least one fourth through hole 150. As shown in the depicted embodiment, the at least one fourth through hole 150 may be, for example, one through hole 150 positioned superior to the through holes 148. In addition, the through hole 150 may be positioned, for example, offset from each of the through holes 148 and between the first side 120 and the second side 122 of the plate 110. The through hole 150 may also be positioned between the anterior most portion of a first through hole 148 and the posterior most portion of a second through hole 148. The distal portion 130 may extend away from the body portion 124 inferior to the second engagement opening 160 and the second alignment opening 162.

Referring now to FIGS. 11-18 and 23-29, a fusion system or ankle fusion plate system 100 is shown. The fusion system 100 may include an implant, plate or bone plate 110, a first alignment guide or proximal alignment guide 200, and a second alignment guide or distal alignment guide 300. The fusion system 100 may also include crossing screws or fasteners 410, 412 and bone screws 414, 416, 418, 420, as shown in FIGS. 23-29. The first alignment guide 200 may be coupled to the plate 110 for insertion of a first fastener 410 across a joint without contacting the bone screws 414, 416, 418, 420 inserted through the plate 110. The first alignment guide 200 may engage the first engagement opening 138 and first alignment opening 140. The first alignment guide 200 may extend away from the plate 110, for example, along the first line 164. The second alignment guide 300 may be coupled to the plate 110 for insertion of a second fastener 412 across a joint without contacting the bone screws 414, 416, 418, 420 inserted through the plate 110. The second alignment guide 300 may engage the second engagement opening 160 and second alignment opening 162. The second alignment guide 300 may extend away from the plate 110, for example, along the second line 166. The first alignment guide 200 and the second alignment guide 300 are also positioned for the first fastener 410 to be inserted without contacting the second fastener 412 and vice versa. Each component of the fusion system 100 may be made from, for example, a biocompatible material, including but not limited to a metal, polymer, composite, etc.

Figure 19:
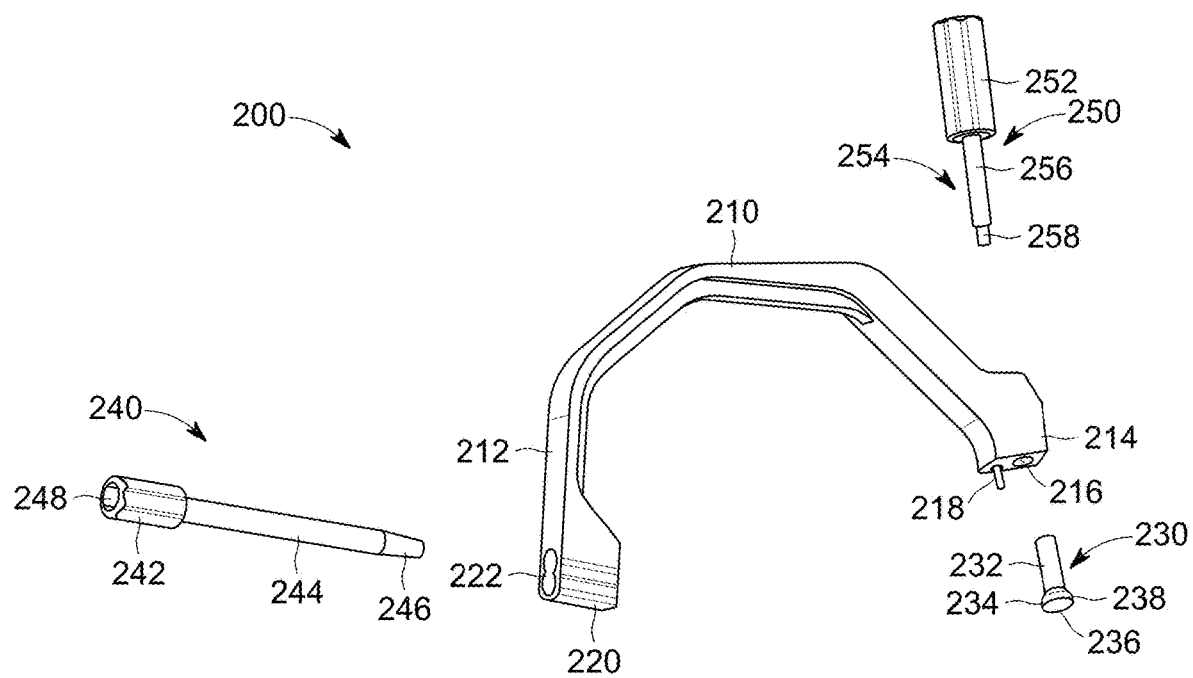
FIG. 19 is an exploded, first perspective view of a first alignment guide of the fusion system of FIG. 11, in accordance with an aspect of the present disclosure.
Figure 20:
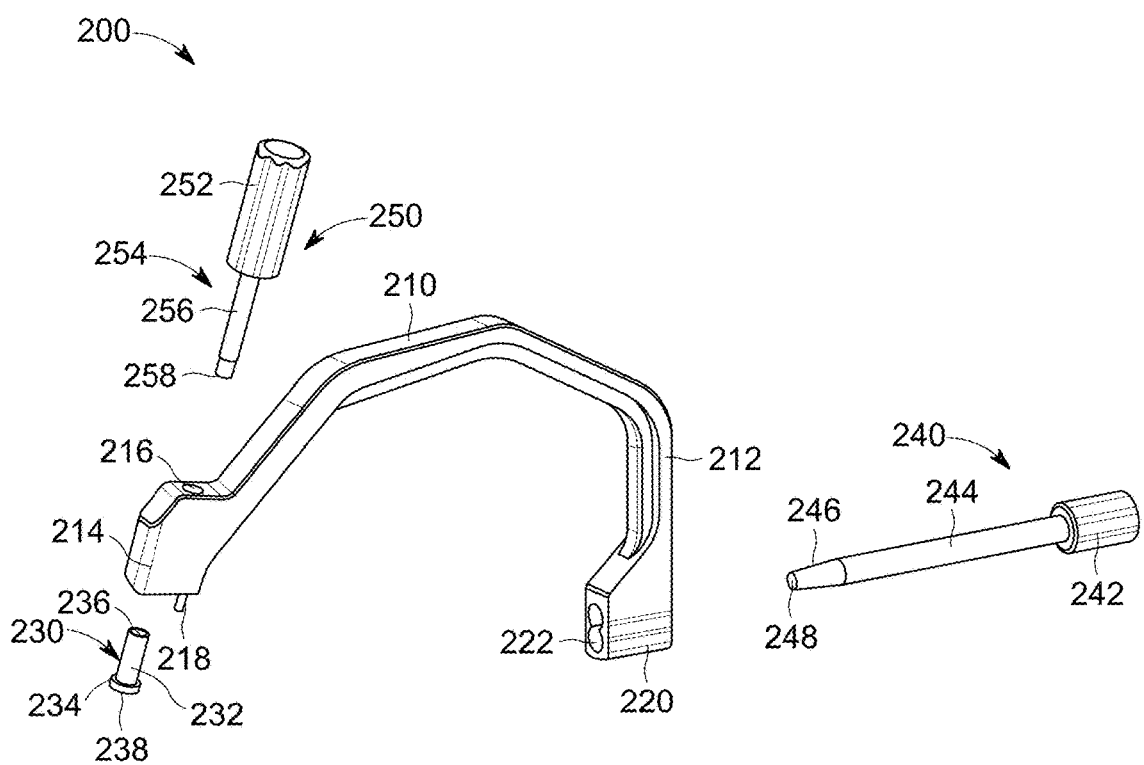
FIG. 20 is an exploded, second perspective view of the first alignment guide of the fusion system of FIG. 19, in accordance with an aspect of the present disclosure.

Referring now to FIGS. 11-20, more specifically FIGS. 19 and 20, the alignment guide 200 is shown. The alignment guide 200 may be coupled to the plate 110 for insertion of the fastener 410 across a joint without contacting the fasteners or screws 414, 416, 418, 420 inserted through the plate 110. The alignment guide 200 may include a body 210, a coupling member 230, and a guide pin tissue protector 240. The alignment guide 200 may also include a fixation member 250 for securing the alignment guide 200 and coupling member 230 to the plate 110. The fixation member 250 and coupling member 230 may be received in a first end of the body 210 and the guide pin tissue protector 240 may be received in a second end of the body 210. The alignment guide 200 may also include at least one guide wire or pin (not shown) for insertion through the guide pin tissue protector 240.

As shown in FIGS. 19-20, the body 210 may include an arm 212 with an attachment portion 214 at the first end of the body 210 and an alignment portion 220 at the second end of the body 210. The attachment portion 214 may include a through hole 216 extending through the attachment portion 220 near the first end. The attachment portion 220 may also include a peg or alignment pin 218 extending away from a bottom surface of the attachment portion 214. The through hole 216 may be positioned adjacent to the alignment pin 218. The alignment pin 218 may be, for example, sized and shaped to engage the alignment opening 140 of the plate 110. The bottom surface of the attachment portion 214 may be, for example, a flat surface for engaging the coupling member 230.

The alignment portion 220 may include at least one hole 222, as shown in FIGS. 19-20. The at least one hole 222 may be, for example, two holes 222 and the holes 222 may partially overlap each other, as shown in the depicted embodiment. The two holes 222 may be positioned linearly as the alignment portion 220 extends away from the arm 212. The holes 222 may be, for example, straight or angled to a desired insertion position as the holes 222 extend through the arm 212 of the body 210. In the depicted embodiment, the holes 222 extend through the alignment portion 220 parallel to each other. The holes 222 may be, for example, sized and shaped to receive the shaft portion 244 of the guide pin tissue protector 240.

With continued reference to FIGS. 19-20, the coupling member 230 includes a shaft 232 and a head 234 positioned at a first end of the coupling member 230. The head 234 may have, for example, an outer diameter that is larger than the outer diameter of the shaft 232. A bottom surface of the head portion 234 of the coupling member 230 may be, for example, curved, arced, or otherwise shaped to match the shape of a top surface of the plate 110 where the head portion 234 engages the plate 110. The coupling member 230 may also include a through hole 236 extending through the coupling member 230 along the longitudinal axis. As shown in FIGS. 19-20, the coupling member 230 may also include a recessed region 238 extending into the head 234 from the first end. The exterior diameter of the shaft 232 of the coupling member 230 corresponds to the interior diameter of the through hole 216 of the alignment guide 200. Further, the exterior diameter of the first portion 256 of the fixation member 250 may correspond to the interior diameter of the through hole 236 of the coupling member 230 allowing for the shaft 254 of the fixation member 250 to pass through the through hole 236 of the coupling member 230. In addition, the exterior diameter of the head 234 of the coupling member 230 may have, for example, a diameter larger than the diameter of the through hole 216 of the alignment guide 200.

As shown in FIGS. 19 and 20, the guide pin tissue protector 240 may include a handle portion 242 and a shaft portion 244 extending away from the handle portion 242. The handle portion 242 may be coupled to the first end of the shaft portion 244 and a tip 246 may be positioned at the second end of the shaft portion 244. The shaft portion 244 may taper at the second end to form the tip 246. The guide pin tissue protector 240 may also include a through hole or cannulation 248 extending from the first end to the second end to enable a guide wire (not shown) to pass through the tissue protector 240 and engage a patient's bone.

As shown in at least FIGS. 19 and 20, the fixation member 250 may include a knob 252 and a shaft 254 extending away from a bottom surface of the knob 252. The shaft 254 may include a first portion 256 extending away from the knob 252 and at least one engagement member 258 for coupling to the engagement opening 138 of the plate 110. The at least one engagement member 258 may be, for example, positioned at an end of the first portion 256 opposite the knob 252. The engagement member 258 may be, for example, threaded to engage corresponding threads in the opening 138 of the plate 110, as shown in the depicted embodiment, deformable to be removably press fit into the opening 138 in the plate 110, or another similar configuration that achieves a coupling of the alignment guide 200 to the plate 110.

Figure 21:
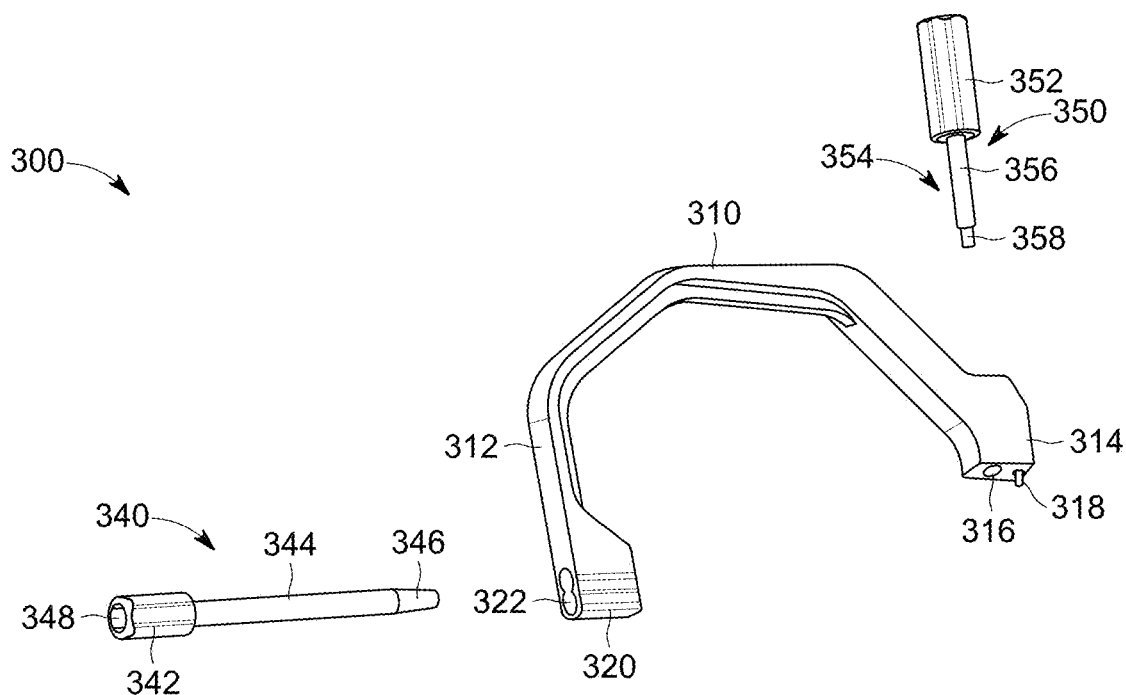
FIG. 21 is an exploded, first perspective view of a second alignment guide of the fusion system FIG. 11, in accordance with an aspect of the present disclosure.
Figure 22:
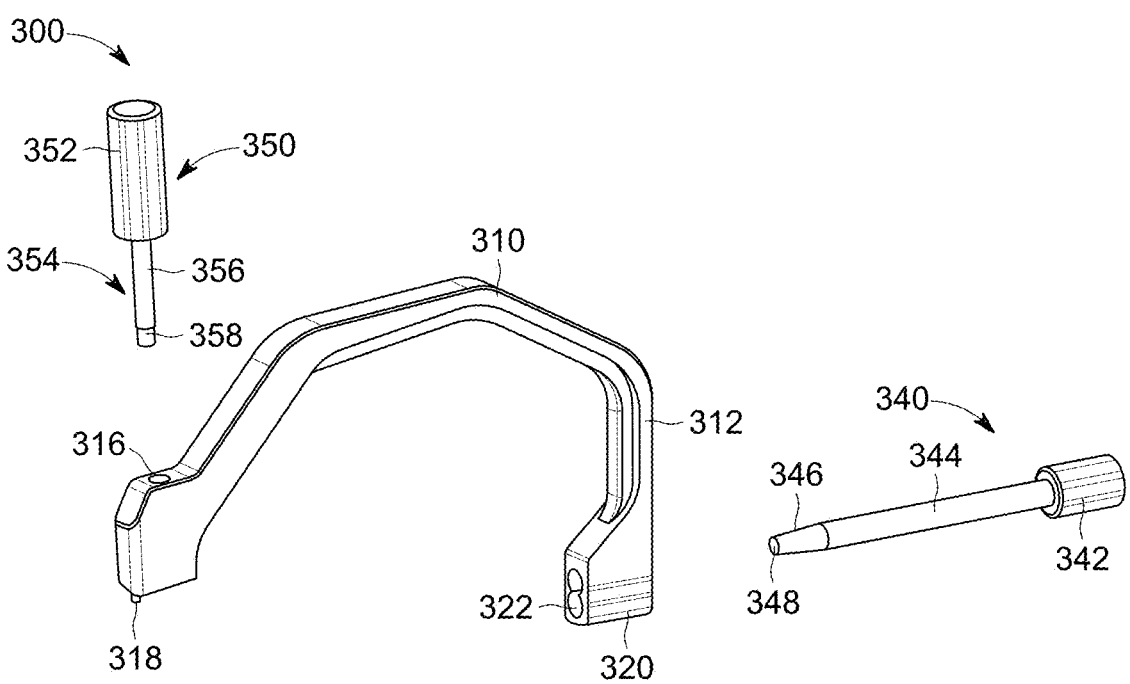
FIG. 22 is an exploded, second perspective view of the second alignment guide of the fusion system of FIG. 11, in accordance with an aspect of the present disclosure.
Figure 23:
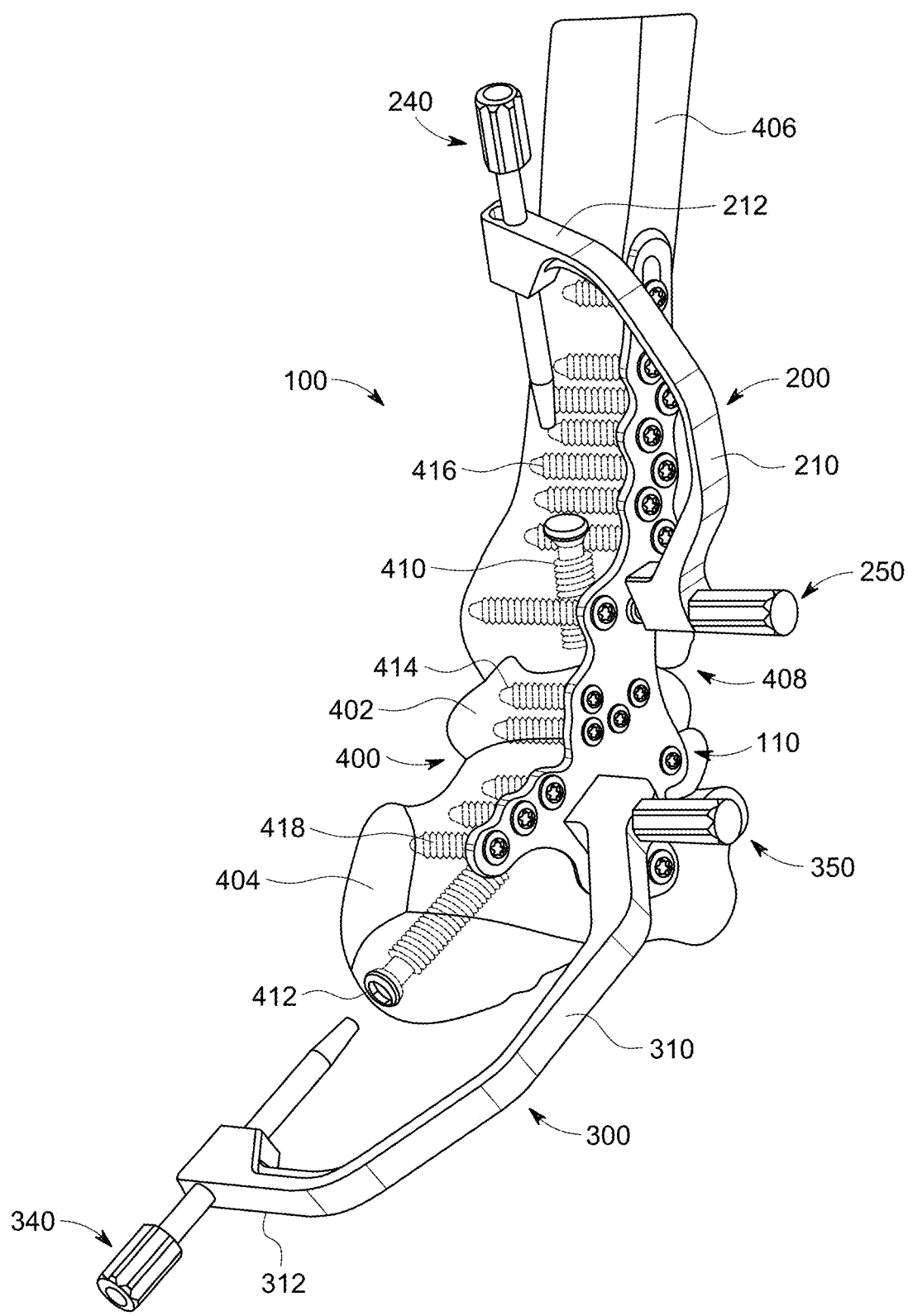
FIG. 23 is a posterior perspective view of a portion of a patient's leg and foot with a fusion system coupled to the bones and including two crossing-screws in a first position, in accordance with an aspect of the present disclosure.
Figure 24:
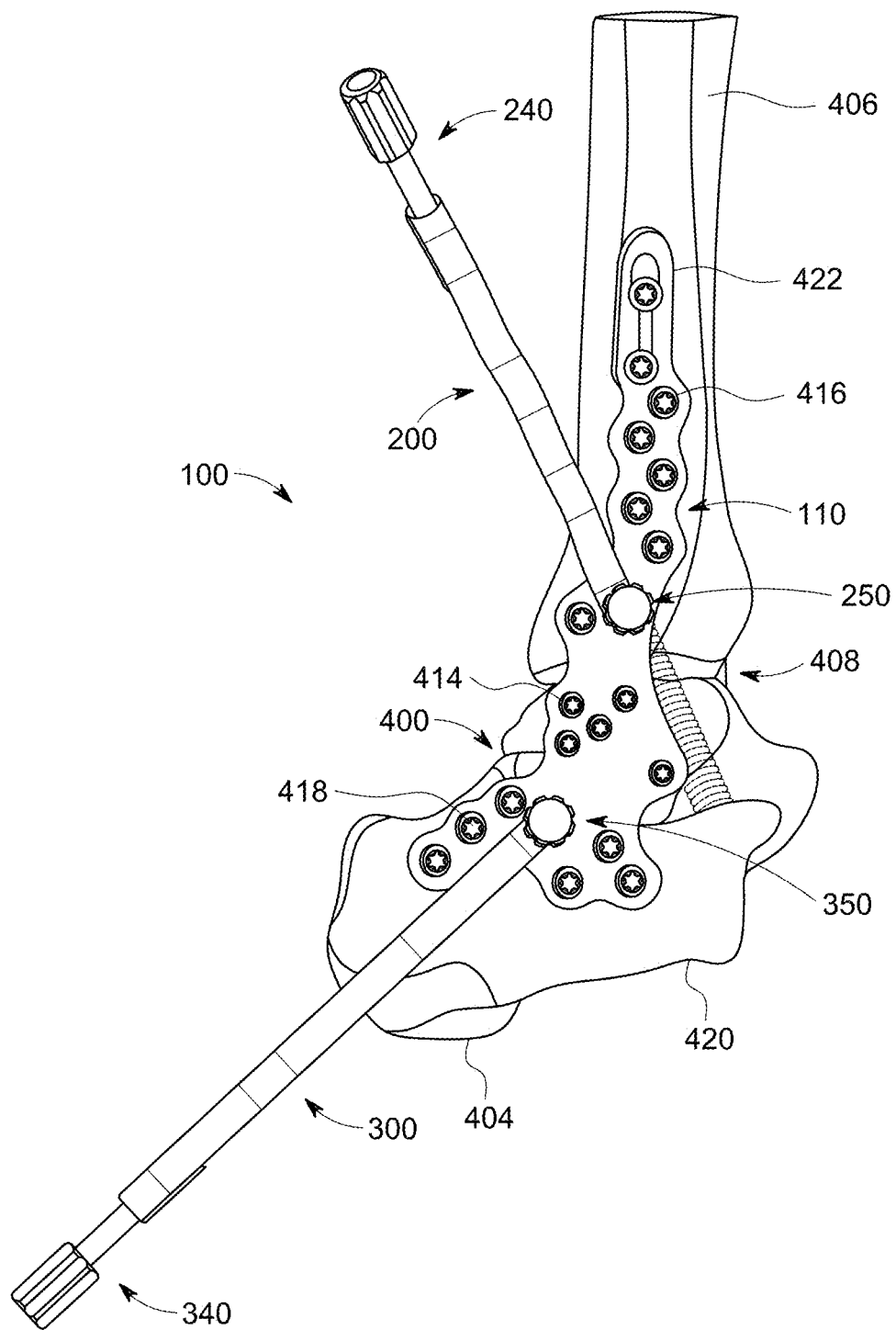
FIG. 24 is a lateral view of the portion of a patient's leg and foot of FIG. 23, in accordance with an aspect of the present invention.
Figure 25:
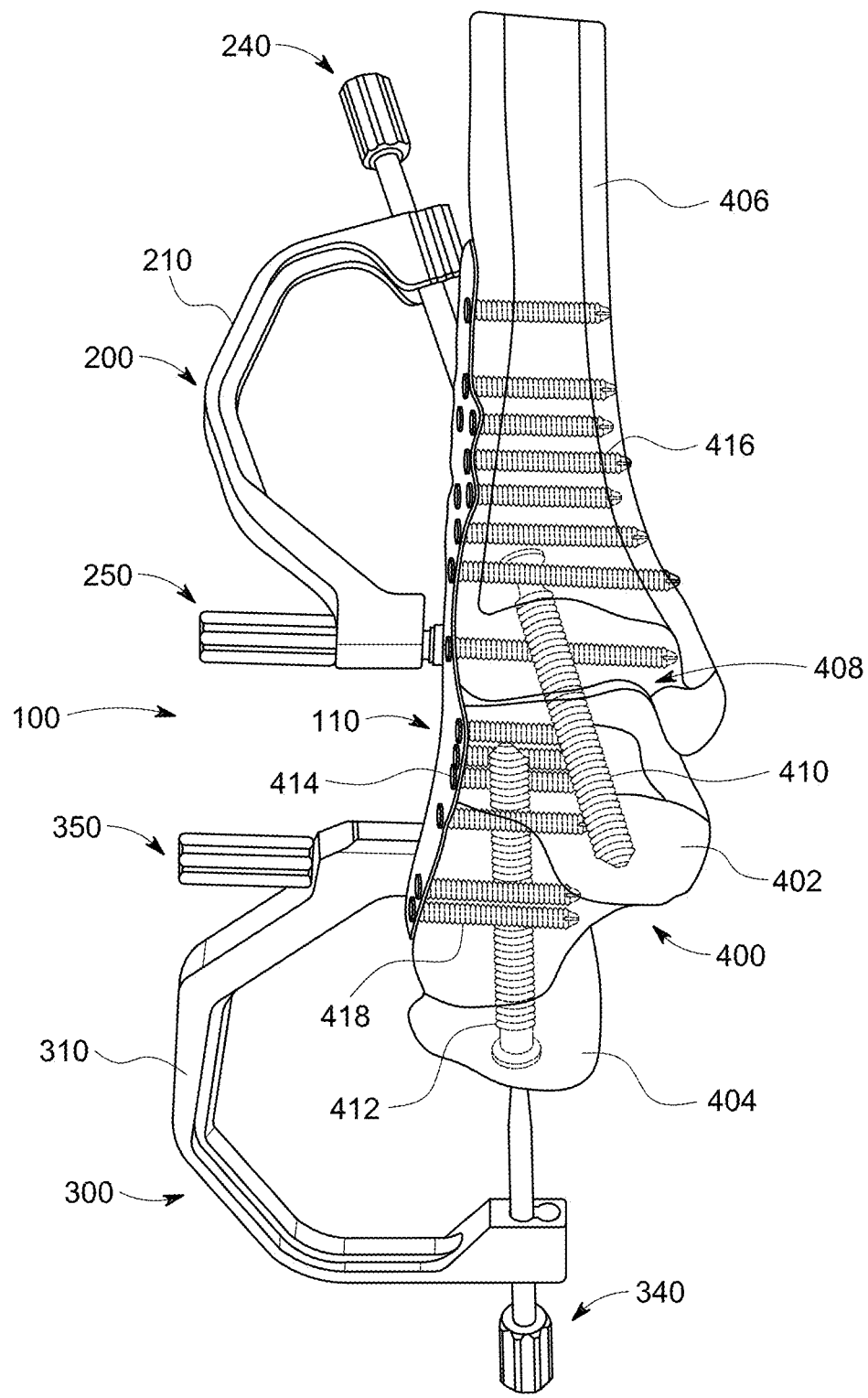
FIG. 25 is an anterior view of the portion of a patient's leg and foot of FIG. 23, in accordance with an aspect of the present disclosure.
Figure 26:
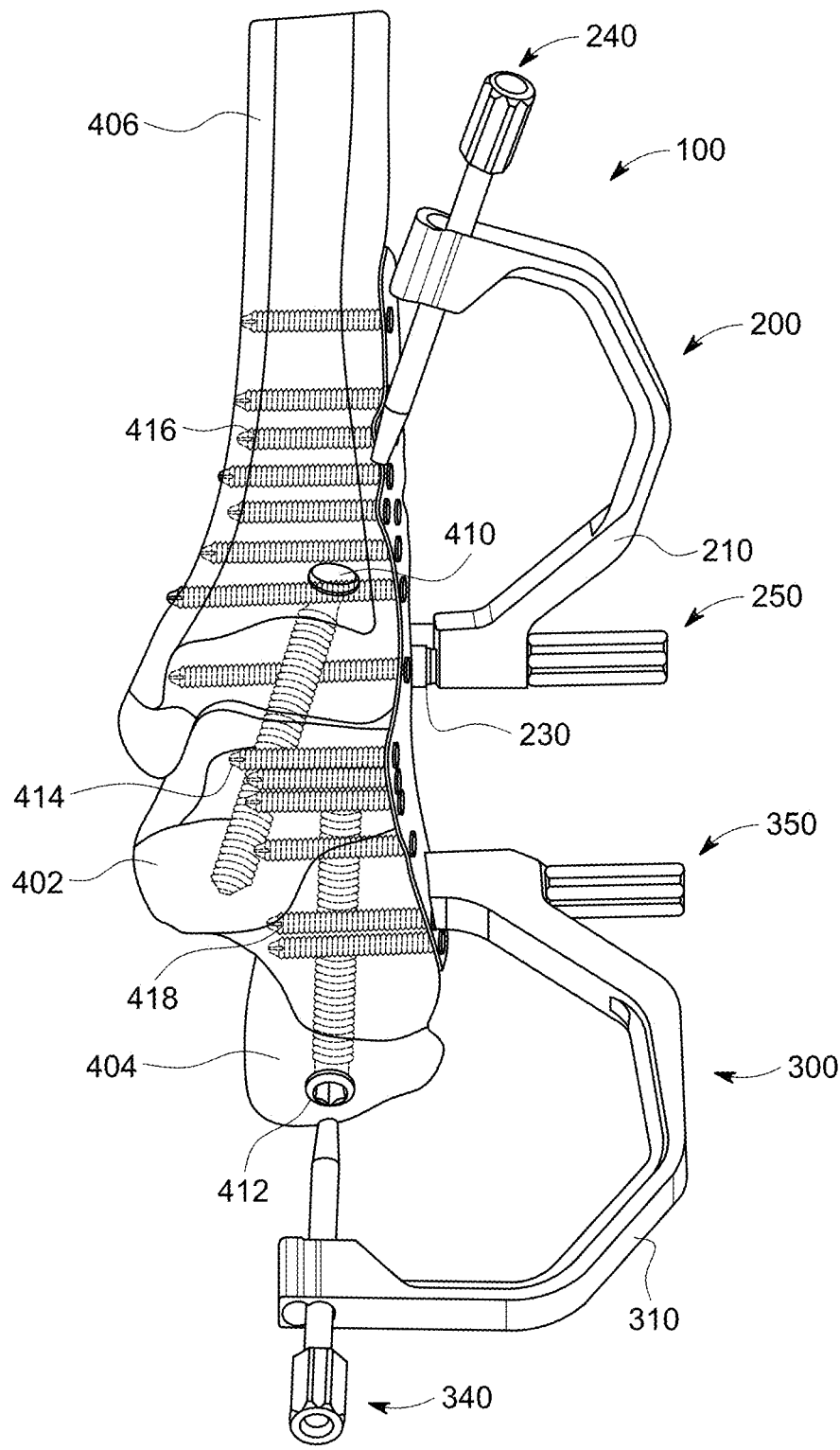
FIG. 26 is a posterior view of the portion of a patient's leg and foot of FIG. 23, in accordance with an aspect of the present disclosure.

Referring now to FIGS. 11-18 and 21-22, more specifically FIGS. 21 and 22, the alignment guide 300 is shown. The alignment guide 300 may be coupled to the plate 110 for insertion of the fastener 412 across a joint without contacting the fasteners or screws 414, 416, 418, 420 inserted through the plate 110. The alignment guide 300 may include a body 310 and a guide pin tissue protector 340. The alignment guide 300 may also include a fixation member 350 for securing the alignment guide 300 to the plate 110. The fixation member 350 may be received in a first end of the body 310 and the guide pin tissue protector 340 may be received in a second end of the body 310. The alignment guide 300 may also include at least one guide wire or pin (not shown) for insertion through the guide pin tissue protector 340.

As shown in FIGS. 21-22, the body 310 may include an arm 312 with an attachment portion 314 at the first end of the body 310 and an alignment portion 320 at the second end of the body 310. The attachment portion 314 may include a through hole 316 extending through the attachment portion 320 near the first end. The attachment portion 320 may also include a peg or alignment pin 318 extending away from a bottom surface of the attachment portion 314. The through hole 316 may be positioned adjacent to the alignment pin 318. The through hole 316 may be positioned medial the alignment pin 318. The alignment pin 318 may be, for example, sized and shaped to engage the second alignment opening 162 of the plate 110.

The alignment portion 320 may include at least one hole 322, as shown in FIGS. 21-22. The at least one hole 322 may be, for example, two holes 322 and the holes 322 may partially overlap each other, as shown in the depicted embodiment. The two holes 322 may be positioned linearly as the alignment portion 320 extends away from the arm 312. The holes 322 may be, for example, straight or angled to a desired insertion position as the holes 322 extend through the arm 312 of the body 310. In the depicted embodiment, the holes 322 extend through the alignment portion 320 parallel to each other. The holes 322 may be, for example, sized and shaped to receive the shaft portion 344 of the guide pin tissue protector 340.

As shown in FIGS. 21 and 22, the guide pin tissue protector 340 may include a handle portion 342 and a shaft portion 344 extending away from the handle portion 342. The handle portion 342 may be coupled to the first end of the shaft portion 344 and a tip 346 may be positioned at the second end of the shaft portion 344. The shaft portion 344 may taper at the second end to form the tip 346. The guide pin tissue protector 340 may also include a through hole or cannulation 348 extending from the first end to the second end to enable a guide wire (not shown) to pass through the tissue protector 340 and engage a patient's bone.

As shown in at least FIGS. 21 and 22, the fixation member 350 may include a knob 352 and a shaft 354 extending away from a bottom surface of the knob 352. The shaft 354 may include a first portion 356 extending away from the knob 352 and at least one engagement member 358 for coupling to the second engagement opening 160 of the plate 110. The at least one engagement member 358 may be, for example, positioned at an end of the first portion 356 opposite the knob 352. The engagement member 358 may be, for example, threaded to engage corresponding threads in the opening 160 of the plate 110 as shown in the depicted embodiment, deformable to be removably press fit into the opening 160 in the plate 110, or another similar configuration that achieves a coupling of the alignment guide 300 to the plate 110.

Referring now to FIGS. 23-29, the fasteners 410, 412 may be, for example, a compression screw, compression fastener, beam fastener, bone screw, beam screw, fixator, elongate member, rod, lag screw, headless screw, a solid screw, or screw for crossing a joint or fracture. The fastener or screw 410, 412 may include a head portion and a shaft or shank portion extending away from a bottom surface of the head portion 162. The fastener 410, 412 may also include a cannulation or through hole extending from a first end through the head portion and the shaft portion to the second end. The cannulation may be, for example, sized and shaped to receive a temporary fixation or guiding member, such as, a k-wire, guide wire, olive wire, pin, or the like, as known by one of ordinary skill in the art. The head portion may include, for example, a drive feature for receiving a drill or screwdriver to insert the fastener into a patient's bones. The shaft portion of the fastener 410, 412 may include, for example, a threaded portion and a smooth portion along the length of the shaft portion. The length of the threaded portion and smooth portion may, for example, vary depending on the bones the fastener 410, 412 will be inserted into, in the depicted embodiment the threaded portion is longer than the smooth portion. Alternatively, the shaft portion may be, for example, threaded along its entire length. The shaft portion may also include at least one tooth positioned at the end of the shaft portion to assist with insertion of the fastener 410, 412 into a patient's bones.

With continued reference to FIGS. 23-29, bone screws 414, 416, 418, 420 are shown. The screws 414, 416, 418, 420 may be of the type known by one of ordinary skill in the art to secure a bone plate to a patient's bones. The screws 414, 416, 418, 420 may include a head portion for engaging the through holes 136, 142, 148, 158 in the plate 110 and a shaft portion for engaging a patient's bone. The shaft portion may be, for example, at least partially threaded along its length. Each of the screws 414, 416, 418, 420 may be different lengths based on the insertion position and the thickness of the bone the screws 414, 416, 418, 420 are being inserted into.

Referring now to FIGS. 23-29, a portion of one embodiment of a surgical method of using the fusion system 100 is shown. The method may include exposing at least one joint 400, 408 and preparing the joint 400, 408. Exposing the joint 400, 408 may include making an incision. Exposing the joint 400, 408 may include, for example, making an initial incision through the skin only. Next, the nerves should be identified and retracted as needed. The surgeon should then continue to expose the joint 400, 408 retracting tendons as necessary. In addition, exposing the joint 400, 408 may include fibular resection in the form of an osteotomy or reaming of the fibula to expose the tibiotalar and subtalar joint. Dissection of the anterior and posterior capsule may be necessary to mobilize the tibiotalar joint and resection osteophytes. Next, any osteophytes on the tibia 406 and talus 402 may be removed to allow for exposure to the ankle joint and facilitate entry of instrumentation for cartilage removal. The method may then include joint preparation based on surgeon preference, as known by one of ordinary skill in the art.

The method may then optionally include temporarily fixing the ankle joint 408 and subtalar joint 400. The ankle joint 408 and subtalar joint 400 may be fixed by placing wires or other fasteners across the ankle joint 408 and subtalar joint 400. Next, the method may then include obtaining a fusion plate 110. The proximal aspect of the plate 110 may be positioned on the tibia 406. Next, the method may include securing the plate 110 using a temporary fixator, for example, a long olive wire in the tibia and temporary fixators, for example, short olive wires in the talus 402 and calcaneus 404. After the plate 110 is temporarily secured to the bones 402, 404, 406, the position of the plate 110 may be confirmed using fluoroscopy.

Then, the method may also include preparing the talus 402 for inserting screws 414 through the at least one first through holes 136 in the body portion 124 of the plate 110. The method may also include obtaining a drill guide (not shown) and inserting the drill guide into the first through holes 136 aligned with the talus 402. Next, a drill (not shown) may be inserted through the drill guide and into the talus 402. After drilling an opening in the talus 402, the drill and drill guide may be removed from the through hole 136 and a depth gauge (not shown) may be inserted into the drilled opening to measure the screw length for insertion into the drilled opening. Once the screw length is determined, a first screw 414 may be inserted through the through holes 136 and into the talus 402 using, for example, a screwdriver (not shown). Each of the first screws 414 may be, for example, partially inserted into the holes 136 until all the other first screws 414 are inserted into their holes 136. Then each of the first screws 414 may then be fully tightened and seated to secure the plate 110 to the talus 402.

Next, the method may include obtaining a compression slot drill guide (not shown) and inserting the drill guide into the slot 144 of the plate 110 on the tibia 406. The drill guide may include, for example, an arrow which may point toward the tibiotalar joint 408. Next, a drill (not shown) may be inserted through the drill guide and an opening may be drilled into the tibia 406. The method may further include removing the drill guide from the plate 110 and measuring the drilled opening with a depth gauge to determine the screw length for a compression screw 422. The compression screw 422 may then be inserted through the slot 144 until fully seated, as shown in FIGS. 24-26, 28 and 29. Alternatively, the compression screw 422 may not be fully seated in slot 144. A partially threaded crossing screw can be used prior to tightening the compression screw. Next, the remaining holes 136, 142 may be prepared as described in greater detail above to receive screws 414, 416 for insertion into the tibia 406. Then, the wires (not shown) may be removed from the bones 402, 406. The method may further include inserting screws 418, 420 through the through holes 148, 158 of the plate 110 and into the calcaneus 404 using the method described in greater detail above, which will not be described again here for brevity sake.

Although not shown, the method may optionally include inserting a plate washer or washer (not shown) in place of at least one screw 414, 416, 418, 420. If a washer is used, the washer should be completely tightened to fully seat and lock the washer within the screw hole 136, 142, 148, 158.

Further, the method may also include inserting a first fastener 410 across the joint 408. With respect to the fastener 410, the terms "fastener," "crossing screw," "bone screw," "fixator," and "screw" may be used interchangeably herein as they essentially describe the same type of device. Inserting the crossing screw 410 may include obtaining an alignment guide 200 and coupling the alignment guide 200 to the plate 110. Alternatively, it is also contemplated that the alignment guide 200 may be coupled to the plate 110 prior to temporarily fixing the plate 110 to the bones 402, 404, 406 to allow for use of a partially threaded screw to be placed prior to plate fixation to achieve compression across the joint via a partially threaded screw. After coupling the alignment guide 200 to the plate 110, the method may include inserting the guide pin tissue protector 240 through the desired hole 222 in the alignment portion 220 of the body 210. The method may then include inserting a wire (not shown) through the tissue protector 240 and across the arthrodesis site in the bones 402, 406. After inserting the wire across the joint 408, the method may include confirming the position and length of the wire using fluoroscopy.

Once the position and length of the wire is confirmed, the alignment guide 200 may be removed from the plate 110. The alignment guide 200 may be removed by detaching the fixation member 250 from the plate 110 and sliding the tissue protector 240 and body 210 off of the guide wire. The method may then include measuring the length of the fastener 410 using a depth gauge (not shown). Next, the method includes drilling over the guide wire using a drill (not shown) and inserting the fastener 410 over the wire and into the bones 402, 406. Next, the method may include confirming the screw length and placement of the screws using fluoroscopy. If the screw length and placement is correct, then the guide wire may be removed.

In addition, the method may also include inserting a second fastener 412 across the subtalar joint 400. With respect to the fastener 412, the terms "fastener," "crossing screw," "bone screw," "fixator," and "screw" may be used interchangeably herein as they essentially describe the same type of device. Inserting the crossing screw 412 may include obtaining an alignment guide 300 and coupling the alignment guide 300 to the plate 110. Alternatively, it is also contemplated that the alignment guide 300 may be coupled to the plate 110 prior to temporarily fixing the plate 110 to the bones 402, 404, 406 to allow for use of a partially threaded screw to be placed prior to plate fixation to achieve compression across the joint via a partially threaded screw. After coupling the alignment guide 300 to the plate 110, the method may include inserting the guide pin tissue protector 340 through the desired hole 322 in the alignment portion 320 of the body 310. The method may then include inserting a wire (not shown) through the tissue protector 340 and across the arthrodesis site in the bones 402, 404. After inserting the wire across the subtalar joint 400, the method may include confirming the position and length of the wire using fluoroscopy.

Once the position and length of the wire is confirmed, the alignment guide 300 may be removed from the plate 110. The alignment guide 300 may be removed by detaching the fixation member 350 from the plate 110 and sliding the tissue protector 340 and body 310 off of the guide wire. The method may then include measuring the length of the fastener 412 using a depth gauge (not shown). Next, the method includes drilling over the guide wire using a drill (not shown) and inserting the fastener 412 over the wire and into the bones 402, 404. Next, the method may include confirming the screw length and placement of the screws using fluoroscopy. If the screw length and placement is correct, then the guide wire may be removed.

Figure 27:
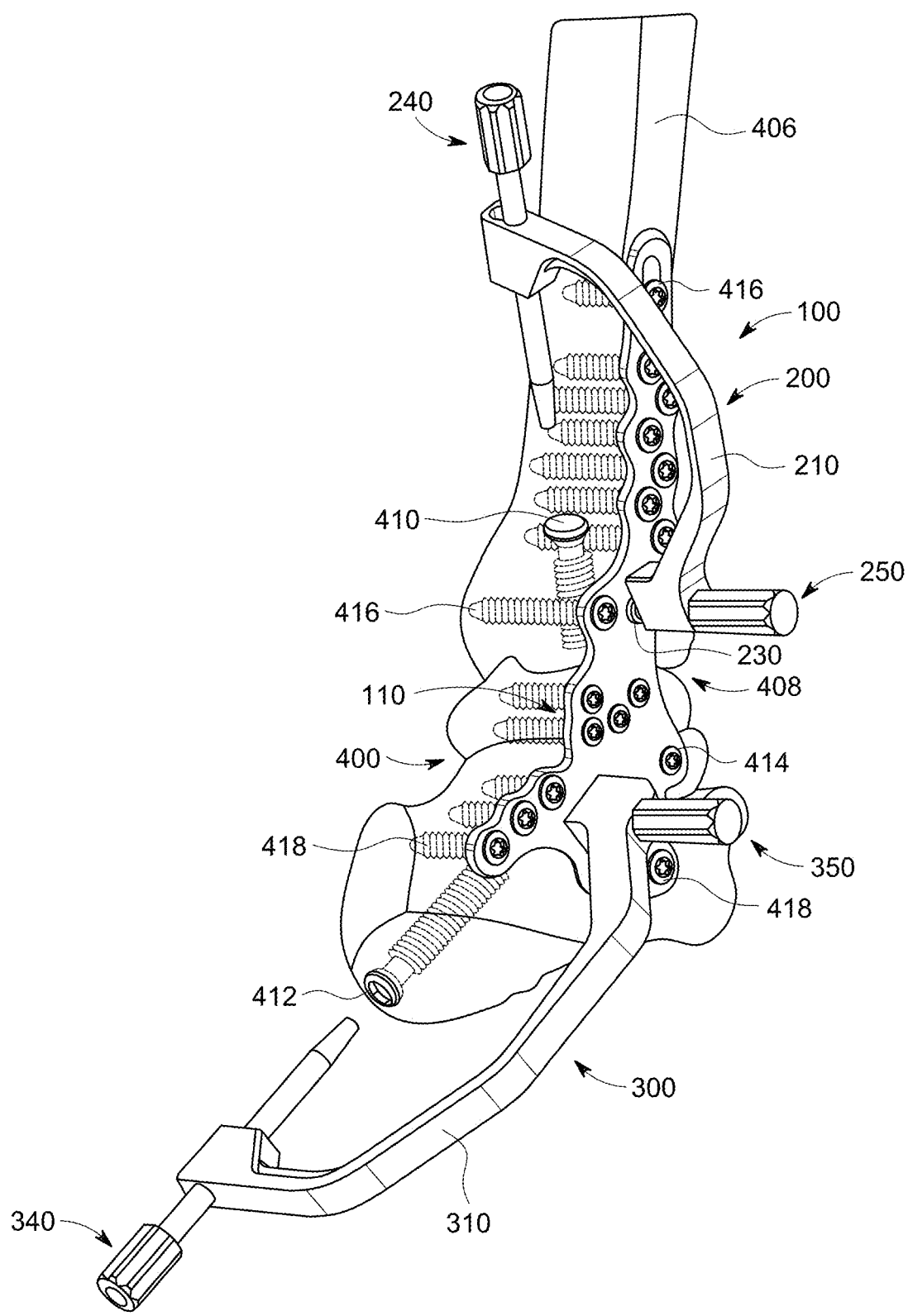
FIG. 27 is a posterior perspective view of a portion of a patient's leg and foot with a fusion system coupled to the bones and including two crossing-screws in a second position, in accordance with an aspect of the present disclosure.
Figure 28:
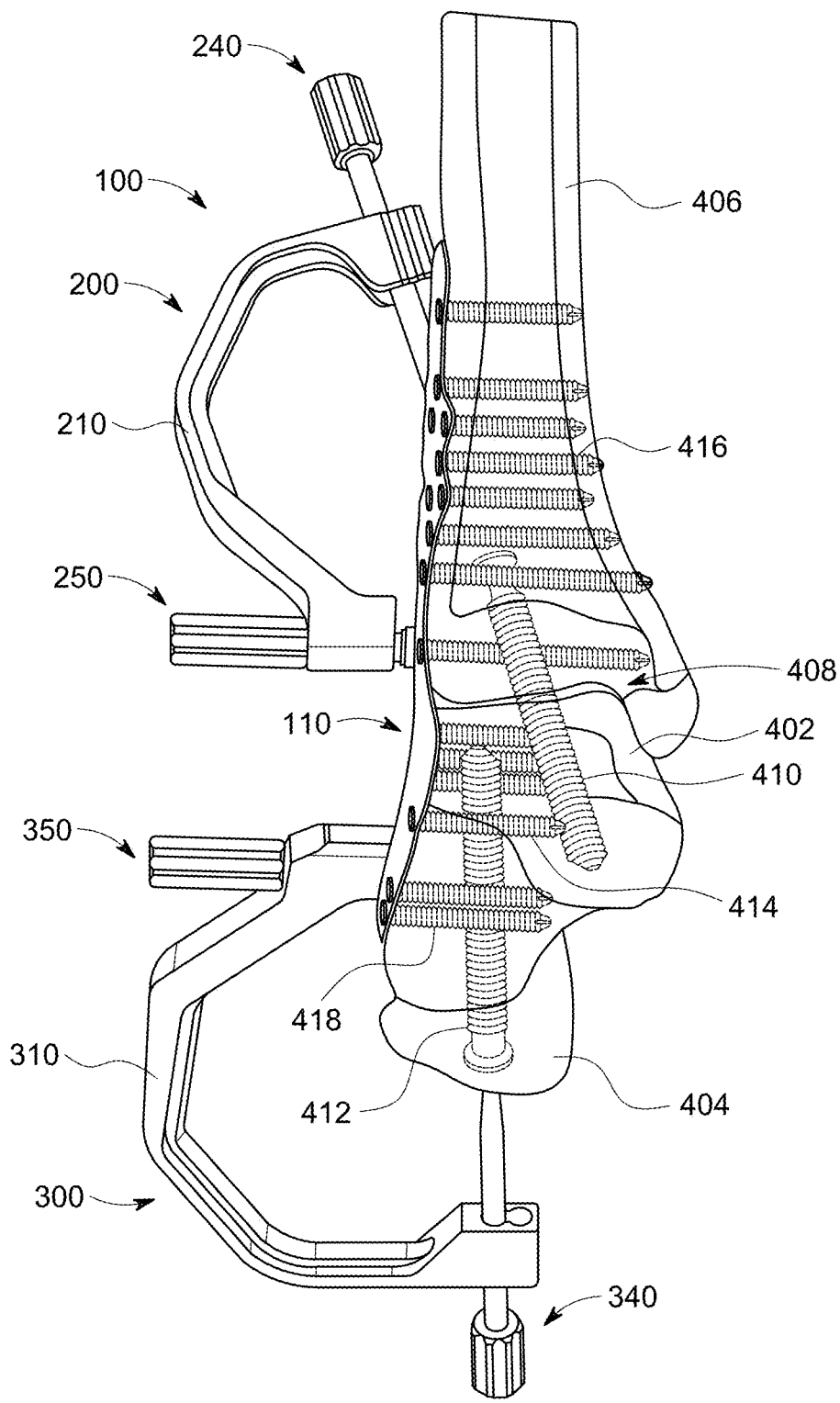
FIG. 28 is an anterior view of the portion of a patient's leg and foot of FIG. 27, in accordance with an aspect of the present disclosure.
Figure 29:
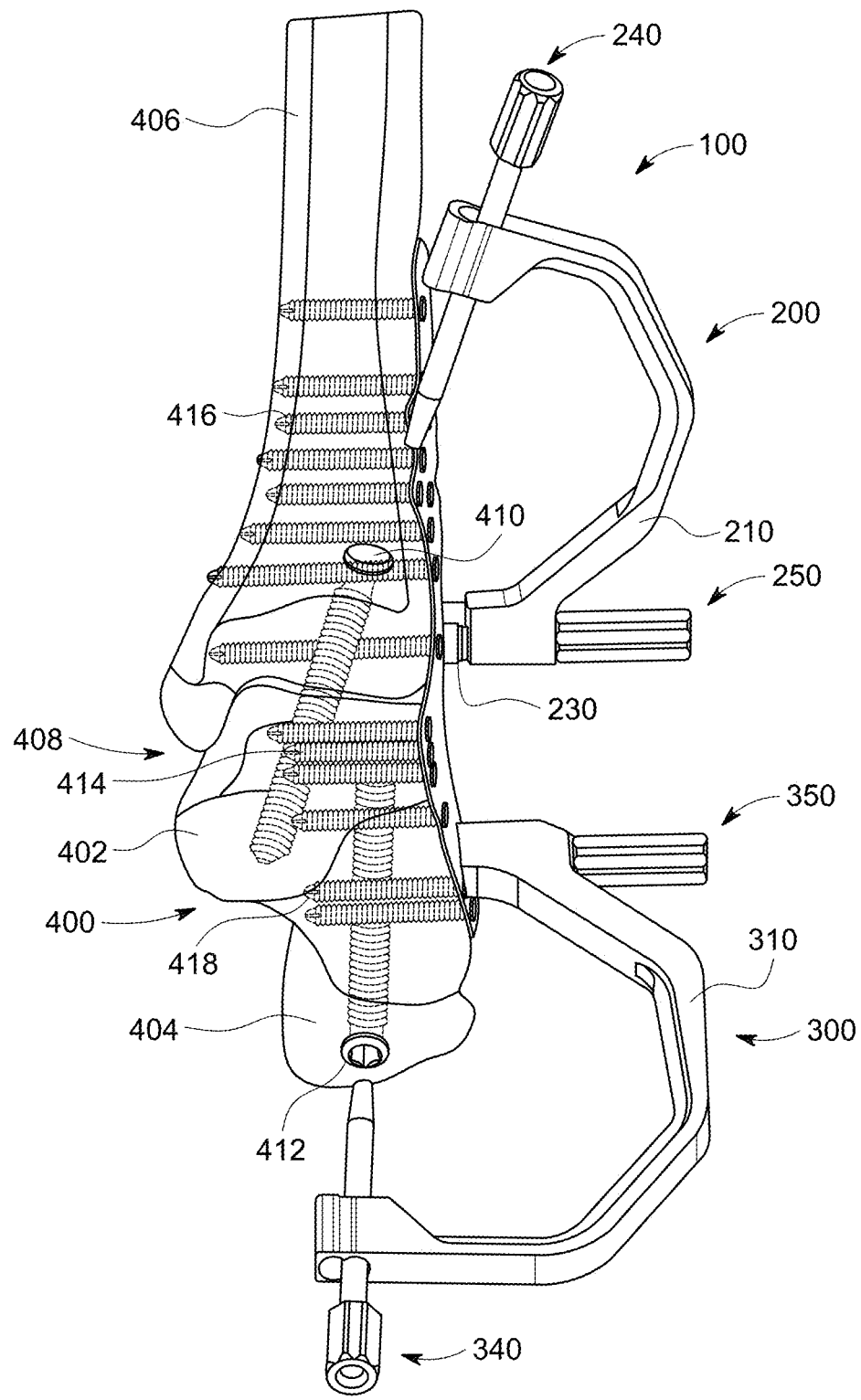
FIG. 29 is a posterior view of the portion of a patient's leg and foot of FIG. 27, in accordance with an aspect of the present disclosure.

The fasteners 410, 412 may be, for example, inserted in either a medial or lateral placement across each joint 400, 408. As shown in FIGS. 23-26, each fastener 410, 412 is inserted in a lateral position. As shown in FIGS. 27-29, each fastener 410, 412 is inserted in a medial position. Finally, the method may include performing incision closure or concomitant procedures.

As may be recognized by those of ordinary skill in the art based on the teachings herein, numerous changes and modifications may be made to the above-described and other embodiments of the present disclosure without departing from the scope of the disclosure. The components of the fusion system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the fusion system may include more or fewer components or features than the embodiments as described and illustrated herein. Accordingly, this detailed description of the currently-preferred embodiments is to be taken in an illustrative, as opposed to limiting of the disclosure.

As may be recognized by those of ordinary skill in the art based on the teachings herein, numerous changes and modifications may be made to the above-described and other embodiments of the present disclosure without departing from the scope of the disclosure. The components of the instruments, guides, implants, plates, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, guides, implants, plates, and/or systems may include more or fewer components or features than the embodiments as described and illustrated herein. For example, the components and features of guides 200, 300 may be used interchangeably and in alternative combinations as would be modified or altered by one of skill in the art. Further, the steps of the surgical methods associated with the guides 200, 300 may be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

Having thus described the preferred embodiments, the disclosure is now claimed to be:

1. A fusion system, comprising:
   a first alignment guide, comprising:
      a body;
      a coupling member engaging a first end of the body;
      a fixation member engaging a first end of the body; and
      a tissue protector engaging a second end of the body;
   a second alignment guide, comprising:
      a body;
      a fixation member engaging a first end of the body; and
      a tissue protector engaging the second end of the body; and
   an implant, wherein the first alignment guide couples to an intermediate portion of the implant and the second alignment guide couples to a distal portion of the implant.

2. The fusion system of claim 1, wherein each body comprises:
   an arm extending from the first end of the body to the second end of the body;
   an attachment portion coupled to the arm at the first end of the body; and
   an alignment portion coupled to the arm at the second end of the body.

3. The fusion system of claim 2, wherein the attachment portion comprises:
   a through hole extending from a top surface of the attachment portion through to a bottom surface of the attachment portion;
   wherein the coupling member is received within the through hole from the bottom surface; and
   wherein the fixation member extends through the coupling member to engage the implant.

4. The fusion system of claim 3, wherein the alignment portion comprises:
   at least one hole extending through the alignment portion from a first end to a second end.

5. The fusion system of claim 4, wherein the at least one hole is two holes, and wherein the two holes at least partially overlap.

6. The fusion system of claim 1, wherein the body comprises:

an arm extending from the first end of the body to the second end of the body;
an attachment portion coupled to the arm at the first end of the body, the attachment portion comprising:
a through hole extending from a top surface of the attachment portion through to a bottom surface of the attachment portion, wherein the fixation member extends through the through hole; and
an alignment portion coupled to the arm at the second end of the body, the alignment portion comprising:
at least one hole extending through the alignment portion from a first end to a second end.

7. The fusion system of claim 6, wherein the at least one hole is two holes, and wherein the two holes at least partially overlap.

8. The fusion system of claim 1, wherein the body of the first alignment guide is positioned at a first angle relative to a longitudinal axis of the implant, wherein the body of the second alignment guide is positioned at a second angle relative to the longitudinal axis of the implant, and wherein the first angle is different than the second angle.

9. The fusion system of claim 8, wherein the implant comprises:
a body portion;
a first extension portion extending away from a first end of the body portion, the first extension comprising:
at least one second through hole; and
a compression slot positioned near a first end of the implant, wherein the at least one second through hole is positioned between the compression slot and the body portion;
a second extension portion extending away from a second end of the body portion, the second extension comprising:
at least one third through hole extending through the implant, wherein the second extension portion extends distally from the body portion; and
a third extension portion extending posteriorly away from the second end of the body portion, the third extension comprising:
at least one fourth through hole extending through the implant, wherein the third extension portion extends posteriorly away from the body portion and second extension portion.

10. The fusion system of claim 9, wherein the body portion comprises:
at least one first through hole;
a first engagement opening for receiving a portion of the fixation member of the first alignment guide; and
a first alignment opening spaced diagonally from the first engagement opening, wherein the first alignment opening receives an alignment pin of the first alignment guide.

11. The fusion system of claim 10, wherein the body portion further comprises:
a second engagement opening for receiving a portion of the fixation member of the second alignment guide; and
a second alignment opening spaced diagonally from the second engagement opening, wherein the second alignment opening receives an alignment pin of the second alignment guide.

12. The fusion system of claim 9, further comprising:
a first fastener, wherein the first fastener engages the first alignment guide to position the first fastener relative to the implant; and a second fastener, wherein the second fastener engages the second alignment guide to position the second fastener relative to the implant.

13. The fusion system of claim 1, wherein the fixation members comprise:
a knob; and
a shaft extending away from the knob, wherein the shaft comprises:
a first portion coupled to and extending away from a second end of the knob;
a second portion coupled to and extending away from the first portion, wherein the first portion includes a first diameter, the second portion includes a second diameter, and the first diameter is larger than the second diameter; and
at least one engagement member coupled to and extending away from the second portion;
wherein the at least one engagement member is threaded to engage threads in an engagement opening in the implant.

14. The fusion system of claim 1, wherein the tissue protectors comprise:
a handle portion;
a shaft portion coupled to and extends from the handle portion;
a tip at a second end of the shaft portion; and
a through hole extending through the handle portion and shaft portion along a longitudinal axis of the tissue protectors;
wherein the tissue protectors extend through at least one hole of an alignment portion of each of the first and second alignment guides.

15. An implant comprising:
a body portion, comprising:
at least one first through hole;
a first engagement opening for receiving a portion of a fixation member of a first alignment guide;
a first alignment opening spaced diagonally from the first engagement opening, wherein the first alignment opening receives an alignment pin of the first alignment guide;
at least one second through hole;
a second engagement opening for receiving a portion of a fixation member of a second alignment guide;
a second alignment opening spaced diagonally from the second engagement opening, wherein the second alignment opening receives an alignment pin of the second alignment guide; and
a compression slot positioned near a first end of the implant, wherein the at least one second through hole is positioned between the compression slot and the body portion;
a first extension portion extending away from a first end of the body portion;
a second extension portion extending away from a second end of the body portion; and
a third extension portion extending posteriorly away from the second end of the body portion.

16. The implant of claim 15, wherein the second extension portion comprises:
at least one third through hole extending through the implant; and
wherein the second extension portion extends distally from the body portion.

17. The implant of claim 16, wherein the third extension portion comprises:

at least one fourth through hole extending through the implant; and wherein the third extension portion extends posteriorly away from the body portion and second extension portion.

18. A method for using a fusion system, comprising:
preparing at least one joint;
inserting fixation wires across the at least one joint;
obtaining a plate;
placing the plate over a first bone and at least one second bone of the at least one joint;
coupling the plate to the first bone and the at least one second bone;
obtaining a first alignment guide;
coupling the first alignment guide to the plate;
inserting a first k-wire through the first alignment guide and across a first joint of the at least one joint;
obtaining a second alignment guide;
coupling the second alignment guide to the plate;
inserting a second k-wire through the second alignment guide and across a second joint of the at least one joint
removing the first alignment guide from the plate;
removing the second alignment guide from the plate;
inserting a first compression fastener across the first joint;
inserting a second compression fastener across the second joint;
removing the k-wire; and
closing an incision.

19. The method of claim 18, wherein coupling the plate to the first bone and the at least one second bone comprises:
inserting at least one first bone screw through a body portion of the plate and into the first bone;
inserting at least one second bone screw through a first extension portion of the plate and into a second bone;
inserting at least one third bone screw through a second extension portion of the plate and into a third bone; and
inserting at least one fourth bone screw through a third extension portion of the plate and into the third bone.

20. The method of claim 19, wherein the first compression fastener is inserted through the first joint without contacting the bone screws; wherein the second compression fastener is inserted through the second joint without contacting the bone screws;
and wherein the second compression fastener is inserted through the second joint without contacting the first compression fastener.

* * * * *